United States Patent [19]

Rebeiz et al.

[11] Patent Number: 5,286,708
[45] Date of Patent: * Feb. 15, 1994

[54] PHOTODYNAMIC HERBICIDAL COMPOSITIONS USING DELTA-AMINOLEVULINIC ACID

[75] Inventors: Constantin A. Rebeiz, Urbana, Ill.; Herbert J. Hopen, Madison, Wis.

[73] Assignee: The Board of Trustees of the University of Illinois, Urbana, Ill.

[*] Notice: The portion of the term of this patent subsequent to Jul. 7, 2009 has been disclaimed.

[21] Appl. No.: 773,030

[22] Filed: Oct. 8, 1991

Related U.S. Application Data

[60] Division of Ser. No. 895,529, Aug. 11, 1986, Pat. No. 5,127,938, which is a continuation of Ser. No. 754,092, Jul. 15, 1985, abandoned, which is a continuation-in-part of Ser. No. 634,932, Jul. 27, 1984, abandoned.

[51] Int. Cl.$^5$ ..................... A01N 43/42; A01N 37/44
[52] U.S. Cl. ..................... 504/130; 504/147
[58] Field of Search ............... 71/113, 65, 84; 504/130, 147

[56] References Cited

U.S. PATENT DOCUMENTS

| | | | |
|---|---|---|---|
| 2,395,446 | 2/1946 | Benson | 71/84 |
| 3,043,675 | 7/1962 | Steinhards et al. | 71/94 |
| 3,274,206 | 9/1966 | Wilbert et al. | 71/94 |
| 3,804,845 | 4/1974 | Moore | 546/259 |
| 3,934,369 | 1/1976 | Rebeiz | 47/58 |
| 4,319,916 | 3/1982 | Abdulla | 71/94 |
| 4,322,241 | 3/1982 | Pissiotas et al. | 71/94 |
| 4,330,321 | 5/1982 | Johnston | 71/94 |
| 4,360,677 | 11/1982 | Doweyko et al. | 546/294 |
| 4,383,850 | 5/1983 | Handte et al. | 71/88 |
| 4,383,851 | 5/1983 | Rogers et al. | 71/94 |

FOREIGN PATENT DOCUMENTS

56845/60 1/1963 Australia .
56849/60 1/1963 Australia .

OTHER PUBLICATIONS

Arrese et al., Current Genetics, 7:175-183 (1983).
Ashton et al., *Mode of Action of Herbicides,* 2nd Ed. (John Wiley & Sons, N.Y.).
Bazzaz et al., Photochemistry and Photobiology, 30:709-721 (1979).
Belanger et al., Spectrochimica Acta, 40A(9):807-827 (1984).
Belanger et al., Biochem., 19:4875-4883 (1980).
Belanger et al., Biochem., Biophys. Res. Comm., 88(2):365-372 (1979).
Belanger et al., Plant Science Letters, 18:343-350 (1980).
Belanger et al., J. Biol. Chem., 257(3):1360-1371 (1982).
Belanger et al., J. Biol. Chem., 257(9):4849-4858 (1982).
Belanger et al., J. Biol. Chem., 255(4):1266-1272 (1980).
Berestetskii et al., CA 93:198884c (1980).
Bickers et al., Biochem. Biophys. Res. Comm., 108(3):1032-1039 (1982).
Bioprocessing Technology, 8(2):3 (Feb. 1986).
Carey et al., Plant Physiol., 79:1-6 (1985).
Carey et al., Plant Physiol., 79:1059-1063 (1985).
Castelfranco et al., Plant Physiol., 53:615-618 (1974).
Castelfranco et al., CA 81:22178p (1974).
Chemical and Engineering News, Sep. 22, 1986, pp. 21-24.
Christensen et al., Br. J. Cancer, 48:35-43 (1983).
Cohen et al., Plant Physiol., 61:824-829 (1978).
Cohen et al., Plant Physiol., 67:98-103 (1981).
Cohen et al., Plant Physiol., 60:743-746 (1977).

(List continued on next page.)

*Primary Examiner*—Richard L. Raymond
*Assistant Examiner*—B. Bembenick
*Attorney, Agent, or Firm*—Curtis, Morris & Safford

[57] ABSTRACT

Herbicidal compositions comprising one or more compounds selected from the group consisting of δ-aminolevulinic acid, inducers of δ-aminolevulinic acid, enhancers of δ-aminolevulinic acid conversion to photodynamic tetrapyrroles, and inhibitors of conversion of divinyl tetrapyrroles to monovinyl tetrapyrroles; and methods of making and using same.

48 Claims, 18 Drawing Sheets

OTHER PUBLICATIONS

Ellefson, Mayo Clin. Proc., 57:454–458 (1982).
*Farming With Pride,* (Pride Company, Inc., P.O. Box 959 Minneapolis, Minn. 55440, 1986), pp. 11–13.
Fletcher et al., Weed Science, 32:722–726 (1984).
Freyssinet et al., Photobiochem. Photobiophys., 1:203–212 (1980).
Gassman et al., CA 83:203948b (1975).
Gough, *Light Stimulated β-Aminolevulinate Accumulation in Luvulinate Treated Barley Seedings,* Carlsberg Res. Comm., 43:497–508 (1978).
Gough et al., CA (7:88590d (1982).
Hardt, CA 87:23068p (1977).
Hendry et al., CA 89:143401e (1978).
*Herbicide Handbook,* Beste, C. E., ed. (Weed Science Soc. of America, Champaign, Ill., 1983), pp. 1–469.
Hoober et al., CA 98:104519r (1982).
Hopen et al., Weeds today, 16(2):4–5 (1985).
Hopf et al., in *The Porphyrins,* vol. 2 (Academic Press, N.Y. 1978), pp. 161–195.
Jurgeson, CA 85:2585y (1976).
Klein eta l., CA 87:164462z (1977).
Klein et al., J. Cell Bio.., 22:443–51 (1964).
Latham et al., Photochem. Photobiol., 37:553–557 (1983).
McCarthy et al., Plant Physiol., 66:142–146 (1980).
McCarthy et al., Biochem. 21:242–247 (1982).
McCarthy et al., Biochem., 20:5080–5087 (1981).
Miller et al., CA 97:141784y (1982).
Oettmeier et al., CA 92:27115w (1975).
Oota, CA 71:109874e (1969).
Orr et al., Plant Physiol., 69:502–507 (1982).
Peacock, in *Fifty Years of Agricultural Research, 1928–1978* (J. Hill, ed.) (Birmingham, Great Britain), pp. 67 ∝ 86.
Ray, CA 79:1230t (1973).
Rebeiz et al., Arch. Biochem. Biophys., 171:549–567 (1975).
Rebeiz et al., Biotech. Bioeng. Symp. No. 12:413–439 (1982).
Rebeiz et al., Botany, 33:225–235 (1984).
Rebeiz, energy Research Symposium (Illinois Agricultural Exp. Station, University of Illinois, Champaign-Urbane, Feb. 5, 1981) pp. 9–12.
Rebeiz et al., in *Regulation of Chloroplast Differentiation,* 389–396 (Allan R. Liss, Inc. 1986).
Rebeiz et al., in *Thirty English Illinois Custom Spray Operators Training Manual* (Symposium, Cooperative Extension Service, University of Illinois, Champaign-Urbana, College of Agriculture, Jan. 8–9, 1986), pp. 91–93.
Rebeiz et al., in *Photosynthesis: Energy Conversion by Plants and Bacteria,* vol. 1 (Academic Press, Inc., 1982), pp. 699–780.
Rebeiz et al., Plant Physiol., 46:543–549 (1970).
Rebeiz et al., Enzyme Microb. Technol., 6:390 (Sep. 1984).
Rebeiz et al., Arch. Biochem. Biophys., 166:446–465 (1975).
Rebeiz, Illinois Research, 16(3):3–4 (1974).
Rebeiz et al., Plant Physiol., 47:24–32 (1971).
Rebeiz et al., Biotech and Bioeng. Symp. 8:453–471 (1978).
Rebeiz et al., Illinois Research, 21(1):3–4 (1979).
Rebeiz et al., Biochem. Biophys. Acta, 590:234–247 (1980).
Rebeiz et al., Plant Physiol., 40:281–286 (1965).
Rebeiz et al., Energy Research Symposium Proc. (University of Illinois, Champaign–Urbana, Apr. 27, 1982), pp. 19–23.
Rebeiz et al., in *Photosynthesis V: Chloroplast Development* (G. Akoyunoglou, ed.) (Balaban International Science Services, Philadelphia, Pa., 1981) pp. 197–212.
Rebeiz, Chemtech., 12:52–63 (1982).

OTHER PUBLICATIONS

Daniell et al., Biochem. Biophys. Res. Comm., 106(2):466–470 (1982).
Daniell et al., Biochem. Bioeng., 26:481–487 (1984).
Daniell et al., Biochem. Biophys. Res. Comm., 104(2):837–843 (1982).
Daniell et al., *Regulation of Chloroplast Differentiation*, 63–70 (Allan R. Liss, Inc. 1986).
Daniell et al., Biochem. Biophys. Res. Comm., 111(2):740–749 (1983).
Dickeson et al., J. Sci. Food Ag., 20:74–77 (1969).
Duggan et al., Biochem. Biophys. Acts, 714:248–260 (1982).
Duggan et al., Plant Science Letters, 24:27–37 (1982).
Duggan et al., Plant Science Letters, 27:137–145 (1982).
Duggan et al., Plant Physiol., 53(2):206–215 (1974).
Duggan et al., CA 80:129154j (1974).
Edwards et al., Neuroscience Letters, 50:169–173 (1984).
Tripathy et al., Progress in Photosynthesis Research IV(8), 439–443, (Biggens, J., ed.). (1987).
Tripathy, J. of Biol. Chem., 261(29):13556–13564 (1986).
Tripathy et al., Anal. Biochem., 149:43–61 (1985).
Vermaas et al., CA 101(7):51954a (1984).
Vlcek et al., CA 91:171842j (1979).
Wegler, *Chemie Der Planzenschutz-Und Schaedlingbekaempfungsmittel*, vol. 5 (Berlin, Germany, 1977), pp. 271–283.
Wu et al., Tetrahedron, 40(4):659–664 (1984).
Wu et al., J. Biol. Chem., 260(6):3632–3634 (1985).

Fig. 2

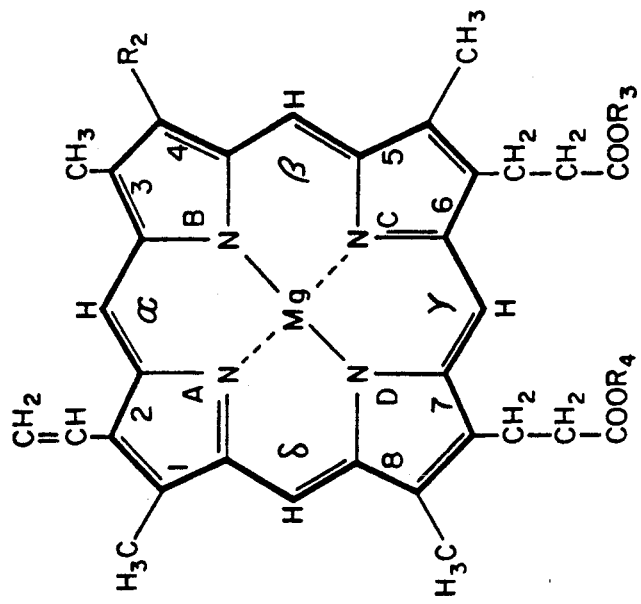

1. Mg PROTO DIESTER, Mg PROTO MONOESTER AND Mg PROTO POOLS

A. $R_2=-CH=CH_2; R_3=-CH_3; R_4=F.Al;$ DV, 7_FAl.E, 6Me.P, Mg PROTO (DV Mg PROTO DIESTER)

B. $R_2=-CH_2-CH_3; R_3=CH_3; R_4=F.Al; 2-MV, 7-FAl.E, 6MeP$ Mg PROTO (MV Mg PROTO DIESTER)

C. $R_2=-CH=CH_2; R_3=-CH_3; R_4=H;$ DV, 7_COOH, 6Me.P, Mg. PROTO (DV Mg PROTO 6ME)

D. $R_2=-CH=CH_2; R_3=H; R_4=Alk;$ DV, 7_Alk.E, 6_COOH, Mg PROTO (DV Mg PROTO 7 ESTER)

E. $R_2=-CH_2-CH_3; R_3=-CH_3; R_4=H, 2-MV, 7-COOH, 6Me.P,$ Mg PROTO (MV Mg PROTO 6ME)

F. $R_2=-CH_2-CH_3; R_3=H; R_4=Alk.2-MV.7Alk.E, 6-COOH,$ Mg PROTO (MV Mg PROTO 7 ESTER)

G. $R_2=-CH=CH_2; R_3=H; R_4=H;$ DV Mg PROTO

H. $R_2=-CH_2-CH_2; R_3=H; = R_4=H; 2-MV$ Mg PROTO

2. PROTOCHLOROPHYLL(iDE)S

A. $R_2 = -CH=CH_2; R_3 = -CH_3; R_4 = F.Al; DV, 7\_F.Al.E, Pchl$
B. $R_2 = -CH_2-CH_3; R_3 = -CH_3; R_4 = F.Al; 2\_MV, 7\_F.Al.E, Pchl$
C. $R_2 = -CH=CH_2; R_3 = -CH_3; R_4 = H; DV, 7\_COOH, 10\_CO_2Me, Pchlide$
D. $R_2 = -CH=CH_2; R_3 = H; R_4 = Alk; DV, 7\_Alk.E, 10\_COOH Pchlide$
E. $R_2 = -CH_2-CH_3; R_3 = -CH_3; R_4 = H, 2\_MV, 7\_COOH, 10\_CO_2Me, Pchlide$
F. $R_2 = -CH_2-CH_3; R_3 = H; R_4 = Alk; 2\_MV, 7\_Alk.E, 10\_COOH Pchlide$

PHOTODYNAMIC HERBICIDAL COMPOSITIONS USING DELTA-AMINOLEVULINIC ACID

This application is a division of application Ser. No. 06/895,529, filed Aug. 11, 1986, now U.S. Pat. No. 5,127,938 issued Jul. 7, 1992 application Ser. No. 06/895,529 is a continuation of application Ser. No. 06/754,092, filed Jul. 15, 1985, now abandoned; and, application Ser. No. 06/754,092 is a continuation-in-part of application Ser. No. 06/634,932, filed Jul. 27, 1984, now abandoned.

The invention described herein was made in the course of work supported by grants from the U.S. Department of Agriculture, the National Science Foundation, and the University of Illinois.

This invention pertains to herbicidal compositions and methods, and more particularly to herbicidal compositions and methods for the induction of the accumulation of photodynamic tetrapyrroles in plants.

The elimination of undesirable plants by herbicides is critical to modern agricultural practice, and a great deal of time and money is currently dedicated to the discovery of efficient, environmentally safe herbicides. Usually this discovery begins with the screening of a spectrum of biochemicals for herbicidal activity. Those chemicals which exhibit promising herbicidal activity are then subjected to further testing, aimed at defining their efficacy, selectivity, environmental impact, and toxic effects on fish, insects and animals. In this scheme, the understanding of the mode of action is irrelevant and is assigned a low priority. As a consequence the detailed mode of action for some of the widely used herbicides is still not completely understood. See, e.g., *Herbicide Handbook*, Beste, C. E., ed. (Weed Science Soc. of America, Champaign, Ill., 1983), pp. 1–469. There is neither a consistent scientific basis for the selection and/or design of safe, effective herbicides, nor a scientific rationale for the systematic elimination of compounds likely to have a deleterious effect on the environment or on non-target plants and animals.

It is therefore a purpose of this invention to provide a model for the systematic design and formulation of herbicides.

It is further a purpose of this invention to provide a class of herbicides which will kill undesirable plants via a predetermined and novel mode of action, based on sound biochemical principles.

It is yet another purpose of this invention to provide herbicides which are environmentally safe, selective, and efficient at low concentrations.

It has now been discovered that compositions comprising δ-aminolevulinic acid and/or inducers of δ-aminolevulinic acid and/or enhances of δ-aminolevulinic acid conversion to photodynamic tetrapyrroles and/or inhibitors of conversion of divinyl tetrapyrroles to monovinyl tetrapyrroles are safe, efficient, selective herbicides, when applied to plants which are subsequently exposed to light. The herbicidal compositions of the present invention result in death and destruction of the plant tissue by a process believed to involve the induced accumulation of photodynamic tetrapyrroles.

The following terms, as used hereinabove and below, have the following meaning unless expressly stated to the contrary: Alk=alkyl group of unknown chain length; ALA=δ-aminolevulinic acid; Chl=chlorophyll; Chlide a=chlorophyllide a; coprogen=coproporphyrinogen; cv=cultivar; dicot=dicotyledenous plant; DP=dipyridyl; DV=divinyl; E=ester; F.Al=fatty alcohol; LWMP=longer wavelength metalloporphyrins (the putative intermediates of ring E formation); M=methylation; ME=methyl ester; Me=methyl; Me.P=methylpropionate; monocot=monocotyledenous plant; MPE=Mg-protoporphyrin monoester; MP(E)=mixture of MPE and Mg-protoporphyrin IX; MV=monovinyl; P=esterification with, followed by stepwise conversion of the latter to phytol; PBG=porphobilinogen; PChl=protochlorophyll; PChlide=protochlorophyllide; Phy=phytol; Proto=protoporphyrin IX; Protogen=protoporphyrinogen; Urogen=uroporphyrinogen, var=variety.

Figure 1:
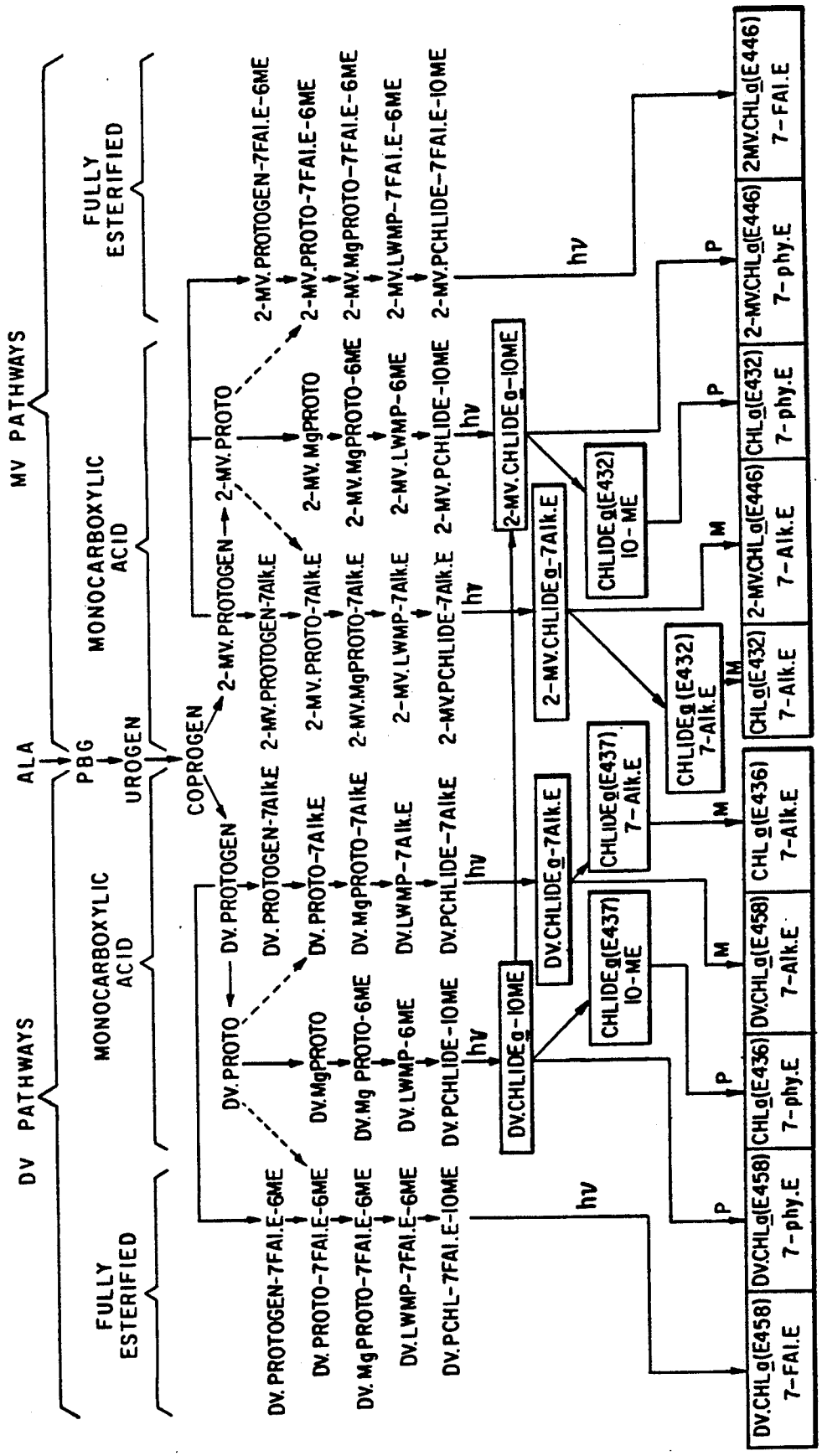
FIG. 1 shows a six-branched Chl a biosynthetic pathway.

The invention will be explained in further detail in conjunction with FIG. 1 (six-branched Chl a biosynthetic pathway) and FIG. 2 (representative structures of some of the metallotetrapyrroles depicted in FIG. 1).

Chlorophyll biosynthesis is a major biological phenomenon in the biosphere and is mandatory for the biosynthesis of photosynthetic membranes during greening and for the repair and maintenance of the Chl in mature green plants. The chlorophylls are a group of Mg-tetrapyrroles which in green plants catalyze the conversion of solar energy into chemical energy via the process of photosynthesis. There are two basic classes of chlorophyll, designated chlorophyll a (Chl a) and chlorophyll b (Chl b); Chl a is involved in the collection of solar energy and its conversion to chemical energy whereas Chl b is believed to be involved only in the collection of solar energy.

Until very recently, it was assumed that in green plants the photosynthetic process was catalyzed by only one species of Chl a, in association with specific lipoproteins of the chloroplast membranes. It has recently been discovered that as many as 10 different species of Chl a may be involved. As shown in FIG. 1, these 10 species of Chl a are all synthesized via a multiple-branched pathway from one common precursor, δ-aminolevulinic aid (ALA), via a series of porphyrin, Mg-porphyrin, and protochlorophyll intermediates, collectively referred to as tetrapyrroles or tetrapyrrole intermediates (see FIG. 2). For a comprehensive review of the chlorophyll synthetic pathways, see Rebeiz, C. A., S. M. Wu, M. Kuhadja, H. Daniell, and E. J. Perkins, Mol. Cell. Biochem. 57:97-125 (1983).

δ-Aminolevulinic acid, a 5-carbon amino acid, is found in most living animal and plant cells and is the primary tetrapyrrole precursor. It is available from a variety of specialty chemical sources, e.g. Sigma Chemical Co., St. Louis, Mo. It is known that excised plant tissues treated in the laboratory with small amounts of ALA will synthesize and accumulate PChlide, which is the immediate precursor of Chlide a and of Chl a, and that ALA will induce the accumulation of earlier tetrapyrrole intermediates of the Chl biosynthetic pathway, such as coproporphyrin, Proto, and MP(E). Once the ALA has stimulated the synthesis of the tetrapyrrole intermediates, they are normally converted in the presence of sunlight into the various forms of Chl a, as described in FIG. 1. However, this rate-limiting conversion does not occur in the dark; without sunlight the tetrapyrrole intermediates accumulate in small amounts in their respective metabolic pools. Upon exposure to light, the conversion to Chl a resumes and the pools are depleted.

In 1974, Castelfranco, P. A., P. M. Rich, and S. I. Beal, Plant Physiol. 53:615-618 noticed while studying the lag phase in greening of etiolated tissue that excised cucumber cotyledons soaked in ALA for 16 hours in the dark underwent visible tissue damage upon subsequent exposure to light, which they attributed to tetrapyrroles formed from exogenous ALA. This phenomenon was regarded as a nuisance to be avoided by illumination with red light of very low intensity or by illumination with intermittent light. Until the present invention, it was believed that the accumulation of tetrapyrroles due to exogenous ALA was a phenomenon attributable to the peculiar circumstances of etiolation. Indeed, once the greening of etiolated tissue is initiated, the biosynthesis of chlorophyll proceeds at an abnormally high rate not found in normal green tissue.

It has now been discovered that living green plants can be induced by exposure to exogenous ALA to accumulate artificially high amounts of photodynamic tetrapyrrole intermediates in excess of levels normally found in living plants, and that such induced artificially high levels are sufficiently photodynamic so that subsequent exposure of the induced plants to sunlight is lethal. This is surprising, since whole green plants synthesize chlorophyll only at a rate sufficient to keep up with leaf expansion and repair, and it was not previously believed that this rate would be sufficient to allow accumulation of lethal amounts of tetrapyrroles.

It is believed that the accumulated tetrapyrroles photosensitize the formation of singlet oxygen, which is a very strong oxidant. The singlet oxygen rapidly oxidizes the lipoprotein components of the plant cellular membranes, thus setting in motion a highly destructive free-radical chain reaction, which can be summarized as follows (hv=photon of light; $^1Tet$=tetrapyrrole in the singlet ground state; $^3Tet^*$=tetrapyrrole in the triplet excited state; $^3O_2$ =oxygen in the triplet ground state; $^1O_2^*$=oxygen in the singlet excited state; UMLP=unsaturated membrane lipoproteins):

1) $^1Tet + hv \rightarrow {}^3Tet^*$
2) $^3Tet^* + {}^3O_2 \rightarrow {}^1Tet + {}^1O_2^*$
3) $^1O_2^* + (UMLP) \rightarrow$ hydroperoxides
4) hydroperoxides→free radicals
5) free radicals+UMLP→more hydroperoxides
6) repetition of steps (4) and (5) until most of the UMLP are oxidized Photosensitization by injected tetrapyrroles has been described in animals and human tissues [see, e.g., Ellefson, R. D., Mayo Clinic Proc. 57:454–458(1982); Christensen, T., T. Sandquist, K. Feren, H. Waksvik, and J. Moan, Br. J. Cancer 48:35–43(1983); Hopf, F. R., and D. G. Whitten, in *The Porphyrins*, Vol. 2, Dolphin, D., ed. (Academic Press, New York, 1978), pp. 161–195; Sandberg, S., I. Romslo, G. Hovding, and T. Bjorndal, Acta Dermatovener (Stockholm) Suppl. 100:75–80(1982); Latham, P. S., and J. R. Bloomer, Photochem. Photobiol. 37:553–557(1983); Bickers, D. R., R. Dixit, and H. Mukhtar, Biochim. Biophys. Res. Comm. 108:1032–1039 (1982)] but this phenomenon has not previously been demonstrated in whole green plants nor adapted to selectively kill undesirable susceptible plant species.

It has further been discovered that in addition to exposure to exogenous ALA, exposure of living plants to inducers of ALA will also result in accumulation of massive amounts of photodynamic tetrapyrrole intermediates in the plant tissues. By "inducer of ALA" or "inducer" is meant a compound which, when applied to plants, stimulates the plant to produce a higher than normal amount of endogeneous ALA, which then has the same effect as exogenous ALA described above. Thus, the herbicidal compositions of this invention may comprise one or more inducers of ALA in addition to, or in lieu of, ALA itself. Non-limiting examples of inducers are, e.g., o-phenanthroline 2,2'-elipyridy 1,7-phenanthroline, 4,7-phenanthroline, and phenanthridine, all available from, e.g., Alpha Products, Danvers, Mass. o-Phenanthroline is preferred.

It has been reported that 2,2'-dipyridyl enhances the biosynthesis and accumulation of tetrapyrroles in excised plant tissues; see, e.g., Duggan, J., and M. Gassman, Plant Physiol 53:206–215 (1974) Furthermore and has now been discovered that certain compounds function as enhancers of ALA utilization in whole green plants. By "enhancer of ALA" utilization or "enhancer" is meant a compound which when applied to living whole green plants enhances the capability of the treated plants to convert exogenous or endogenous ALA to photodynamic tetrapyrroles. Thus the herbicidal compositions of the present invention may also comprise one or more enhancers of ALA in addition to, or in lieu of, ALA or inducers of ALA. Non-limiting examples of suitable enhancers are, e.g., 2,2'-dipyridyl (2,2'-DP), 2,3'-dipyridyl (2,3'-DP), 4,4'-dipyridyl (4,4'-DP), pyridine aldehyde, pyridine aldoxime, and picolinic acid, all available from Aldrich Chemical Co., Milwaukee, Wisc. 2,2'-DP, picolinic acid, and pyridine aldehyde are preferred. In cucumber, enhancers includes pyridine 2-aldoxime, pyridine 2-aldehyde, picolinic acid and 4,4'-dipyridyl. Certain compounds which function as inducers in one composition may function as enhancers in another composition or at different concentrations. For example, 2,2'-DP at concentrations of greater than 30 mM is also an inducer.

Figure 2:
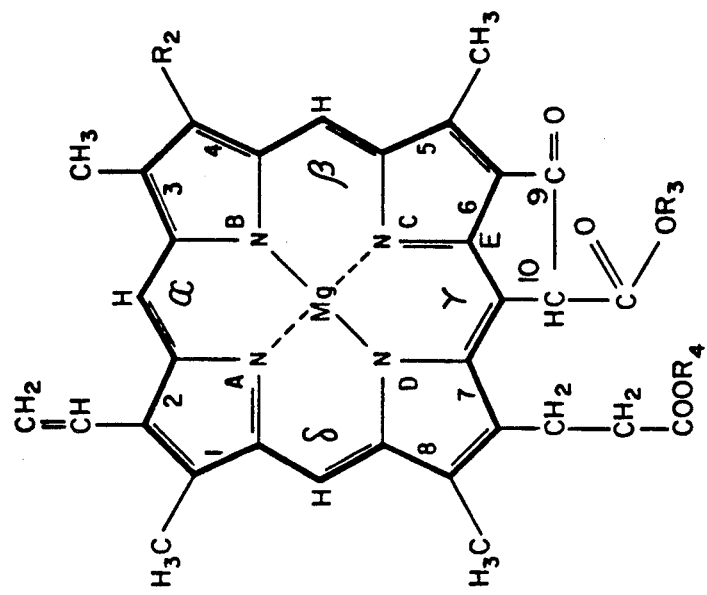
FIG. 2 shows a representative structure of some of the metallotetrapyrroles depicted in FIG. 1.

As can be seen in FIG. 1; three of the branches of the synthetic pathway have been designated as divinyl (DV) pathways; the two monocarboxylic acid pathways are thought to predominate in dicots and in monocots in the presence of light. The remaining three branches have been designated the monovinyl (MV) pathways; the two monocarboxylic acid pathways predominate in monocots in the dark. Plants may be classified as "monovinyl" or "divinyl" plants, depending on which pathways predominate. A monovinyl plant is a plant species which in darkness accumulates MV PChlide via the MV monocarboxylic biosynthetic routes and upon exposure to light initially forms Chl mainly via the MV monocarboxylic acid routes. Divinyl plants are plant species which accumulate mainly DV PChlide in darkness and upon exposure to light initially form Chl preferably via the DV monocarboxylic biosynthetic routes. After several hours in daylight both MV and DV plants appear to form Chl via the DV monocarboxylic routes.

It has been discovered that in DV plant species, the accumulation of artificially high amounts of DV tetrapyrroles or equal or lower levels of MV tetrapyrroles is lethal to the plant upon subsequent exposure to light, while in MV species the reverse is true, i.e., the accumulation of artificially high amounts of MV tetrapyrroles or equal or lower levels of DV tetrapyrroles is lethal upon subsequent exposure to light. It has also been discovered that certain formulations of ALA and/or inducers and/or enhancers favor accumulation of MV tetrapyrroles in MV plants, while other such formulations favor accumulation of DV tetrapyrroles in MV plants. Likewise, certain formulations of ALA and/or inducers and/or enhancers favor accumulation of DV tetrapyrroles in DV plants, while others favor accumulation of MV tetrapyrroles in DV plants. Further, it has been discovered that certain compounds function as DV inhibitors. By "DV inhibitor" or "inhibitor" is meant a compound which, when applied to plants, inhibits the conversion of DV tetrapyrroles to MV tetrapyrroles Non-limiting examples of inhibitors are 2,3'-DP, 2,4'-DP, and 4,4'-DP 2,3'-DP is preferred. Accordingly, by proper selection of suitable formulations of ALA and/or inducers and/or enhancers and/or inhibitors, which selection can readily be made by one skilled in the art, it is possible to preferentially kill MV or DV plant species Further, since different plant species vary in their photodynamic sensitivity, it is possible to select proper formulations to selectively kill one MV plant over another, or one DV plant over another.

The herbicidal compositions of the present invention may also comprise combinations of two or more compounds selected from the group consisting of ALA, inducers, enhancers, and inhibitors, e.g. ALA+one or more inducers, ALA+one or more enhancers, ALA+one or more inhibitors, ALA+one or more inducers+one or more enhancers, ALA+one or more inducers+one or more inhibitors, ALA+one or more enhancers+one or more inhibitors ALA+one or more inducers+one or more enhancer+one or more inhibitors; one or more inducers+one or more enhancers, one or more inducers+one or more inhibitors; one or more enhancers+one or more inhibitors, one or more inducers+one or more enhancers +one or more inhibitors, etc.

The composition may also contain one or more of the following: suitable carrier(s) [e.g. colloidal magnesium aluminum silicate, pumice, talc, or combinations thereof]; solvent(s) [e.g. water, 0.45 acetone: 0.45 ethanol:0.1 Tween 80:9 water (v/v/v/v), 0.45 acetone:0.45 methanol:0.1-Tween 80:9 water (v/v/v/v), 0.1-1% Tween 80 in water (v/v), 0.9 polyethylene glycol (PEG):0.1 Tween 80:9 water (v/v/v), 0.1-0.7 PEG:0.2-0.8 methanol:0.1 Tween 80:9 :water (v/v/v/v), 0.9 methanol:0.1 Tween 80:9 water (v/v/v), 0.45 acetone:0.45 ethanol:0.2 Tween 80:0.9 ethylene glycol:18 water (v/v/v/v/v), or one or more of the following: benzene, toluene, xylene, kerosene, 2-methoxyethanol, propylene glycol, diethylene glycol, diethylene glycol diethyl ether, formamide, methylformamide, cyclohexanone, isophorone]; tuffer(s) [e.g. citric acid]; wetting agent(s) [e.g. sodium N-methyl-N-oleoyltaurate, an alkylphenoxy polyoxyethylene ethanol, sodium α-olefin sulfonate, sodium isopropylnaphthalene sulfonate, polyoxyethylated vegetable oil]; dispersing agent(s) [e.g. sodium lignin sulfonate, the sodium salt of a naphthalene sulfonic acid-formaldehyde condensate, hydroxyethyl cellulose]; defoaming agent(s) [e.g. silicone]; emetic(s) [e.g. sodium tripolyphosphate, tetrapotassium pyrophosphate, arecotine, apomorphine, copper sulfate]; stench(es) [e.g. pyridine]; penetrant(s); surfactant(s); emulsifier(s); adjuvant(s) [e.g. phytoblend oils]; and one or more other known herbicides, e.g. Goal TM (Rohm & Haas Co., Philadelphia, Pa.), Lasso TM (Monsanto Colo., St. Louis, Mo.), Roundup TM (Monsanto Colo., St. Louis, Mo.), or Sutan Plus TM (Stauffer Chemical Co., Westport, Conn.). Of course, any such additional component must be compatible with the herbicidal components of the present invention and with the other ingredients in the mixture.

The composition may be formulated in any manner conventionally used for herbicidal preparations., e.g. as a solution, suspension, emulsion, flowable concentrate, emulsifiable concentrate, gel, paste, foam, cream, aerosol, wettable powder, dust, dispersible granules, and the like, according to procedures known to those skilled in the art. Preferably, the composition is a solution, suspension, emulsion, aerosol, flowable or emulsifiable concentrate, or wettable powder. Of course, the formulation must be such that the active ingredient(s) penetrate(s) the plant tissue and translocates to the sites of tetrapyrrole synthesis. When the compositions are made in solution they may conveniently comprise concentrations of from about 2 to about 30 mM ALA and from about 10 to about 30 mM inducer, enhancer, or inhibitor.

The herbicidal compositions of the present invention may be applied topically, e.g. as a dust, soak, dip, spray, mist, or fog, in an amount sufficient to induce the accumulation of photodynamic tetrapyrroles. Alternatively, the herbicidal compositions may be applied to the soil for uptake by plant roots and translocation to the vegetative part of the plant, or as a pre-emergence treatment to prevent seed-germination. The amount of herbicidal composition to be applied will vary, depending on the particular active ingredient(s) selected, but in general will be an amount sufficient to supply from about 10 g to about 15 kg ALA per acre and/or from about 10 g to about 10 kg of an inducer, enhancer, or inhibitor per acre. Means of determining optimum application rates are within the purview of those skilled in the art.

Once the plant has been induced to begin accumulating artificially high amounts of tetrapyrroles by exposure to the herbicidal composition of the present invention, the plant may be shielded from exposure to light to allow maximum tetrapyrrole accumulation. Such dark incubation is not required for activity but tends to optimize efficiency of the herbicidal compositions. The plants can be shielded in any convenient manner, as by wrapping them in dark paper, cloth, or foil, or by placing them in a dark room or container. Under field conditions, the ideal method to provide a period of dark incubation is to apply the herbicidal composition at dusk or during the night, at a time chosen to allow the plants to rest in the dark for at least one hour. It is to be understood that in order to facilitate tetrapyrrole accumulation, the dark need not be total absence of light, but rather substantial absence of light at wavelengths of from 300 to 700 nm. Preferably, the plants are allowed to rest in the dark for from about 1 to about 20 hours. One to 8 hours is particularly preferred.

Thereafter the plants are exposed to about 200 ft. candles or more of light at wavelengths of about 300 to about 700 nm. The light may be supplied by any convenient source, e.g. an incandescent lamp, metal halide lamp, sunlamp, or a cool white or skylight fluorescent bulb. In the field, of course, the preferred source of light is sunlight. The plants are exposed to light for a period of time sufficient to oxidize most of the unsaturated membrane lipoproteins; a period of from about 1 to about 14 days is preferred.

Herbicidal activity is indicated by bleaching of the leaves, stems, and/or nodes, followed by wilting and death. If all the leaf buds are not treated, the plant may recover and require repeated treatment.

A further understanding of this invention can be had from the following non-limiting examples. As used hereinabove and below unless expressly stated to the contrary, all temperatures and temperature ranges refer to the centigrade system and the terms ambient and room temperature refer to about 20°–25° C. The term percent or (%) refers to weight percent and the terms mole and moles refer to gram moles. "Level of significance" refers to the probability that for a population for which the correlation coefficient (r) is equal to zero, a sample of size n can be taken, for which the correlation coefficient equals or exceeds the calculated value of r reported. for the given sample. The abbreviation "n.s." stands for "not significant".

SECTION I

Protocol for Determining Photodynamic Herbicidal Compositions

The following examples describe model systems whereby persons skilled in the art can readily determine photodynamic compounds and compositions useful in the present invention.

Example I

Photodynamic Herbicidal Effects of ALA

Cucumber (*Cucumis sativus* L. cv Beit Alpha MR) seedlings were germinated in the greenhouse in vermiculite in glass containers, 9 cm deep and 9 cm in diameter. The seedlings were watered periodically with Hoagland solution. The photoperiod was maintained at 14 hours of light per day with 50 ft. candles of incandescent light.

Six-day old green seedlings were thinned to 10 plants per container and ALA (Sigma Chemical Co., St. Louis, Mo.) was applied as a fine spray. The ALA was dissolved at concentrations ranging from 0 to 20 mM in a solvent mixture made up of 0.45 acetone:0.45 ethanol:0.1 Tween 80:9 water (v/v/v/v), adjusted to pH 3.5 with dilute HCl. Each 9 cm-diameter glass container (approximately 63.6 $cm^2$ leaf surface area) was sprayed with 0.25 ml of ALA (treated) or 0.25 ml of solvent (control), which is equivalent to a spray rate of about 40 gallons/acre and a field application rate of ALA of about 0 to 524 g/acre. The solutions were delivered as a very fine and uniform spray with a modified Pierce "Quixspray" aerosol spray kit (Pierce Chemical Co., Rockford, Ill.), as follows: 0.25 ml of solution was placed in a sawed-off 10 ml conical centrifuge tube, which was placed inside the Quixspray spray jar. The delivery of a very fine mist was achieved by pumping the solution through a fine bore polypropylene tubing (0.3 mm inside diameter, or 0.5 mm inside diameter for more viscous solutions). One end of the fine-bore tubing was inserted into the Quixspray intake hose, while the other end was dipped into the solution in the conical centrifuge tube. In this manner it took 10–20 sec to deliver 0.25 ml spray, and this in turn provided ample time for thoroughly spraying the seedlings to leaf saturation. Each treatment was performed duplicate.

After spraying, the plants were wrapped in aluminum foil and were placed inside a cardboard box which was wrapped in two layers of black plastic. The dark-boxes were then incubated overnight (17 hours) at 28° C., in order to allow the biosynthesis and accumulation of tetrapyrroles to take place.

The next morning, the treated plants were sampled for their tetrapyrrole content. The plants were taken in the black boxes to a dark room equipped with a green safelight which permits the manipulation of the treated tissues without affecting in any way their tetrapyrrole content. One of each two cotyledons of every two replicates was excised Two- to three-gram batches were then homogenized in a Sorval Omnimixer (DuPont Instruments, Newtown, Conn.) in acetone:0.1 N $NH_4OH$ (9:1 v/v) at a rate of 18 ml of solvent per 3 g of tissue. The resulting 80% acetone extract containing various tetrapyrroles was cleared from lipoproteins and cell debris by centrifugation at 39,000 x g for 10 min at 0° C. Chlorophyll, a fully esterified tetrapyrrole, was removed from the aqueous acetone solution by extraction with hexane according to the method of Rebeiz, C. A., J. R. Mattheis, B. B. Smith, C. C. Rebeiz, and D. F. Dayton, Arch. Biochem. Biophys. 166:446–465(1975). The more polar mono- and dicarboxylic tetrapyrroles such as Proto, MP(E), and PChlide remained in the hexane-extracted aqueous acetone fraction. The chemical structure of these tetrapyrroles has been discussed at length in Rebeiz, C. A. and J. Lascelles, in *Photosynthesis: Energy Conversion by Plants and Bacteria*, Vol. 1, Govindjee, ed. (Academic Press, New York, 1982), pp. 699–780; and Rebeiz, C. A., S. M. Wu, M. Kuhadja, H. Daniell, and E. J. Perkins, Mol. Cellular Biochem. 57:97–125(1983). The amount of Proto, MP(E), and PChlide was determined spectrofluorometrically on aliquots of the hexane-extracted acetone fraction according to the method of Rebeiz, C. A., J. R. Mathheis, B. B. Smith, C. C. Rebeiz, and D. F. Dayton, Arch. Biochem. Biophys. 171:549–567-(1975). A small aliquot of the hexane extract containing the Chl a and b was dried under $N_2$ gas and the residue was redissolved in 80% acetone. The amount of Chl a and b in this acetone solution was then determined spectrofluorometrically according to the method of Bazzaz, M. B., and C. A. Rebeiz, Photochem. Photobiol. 30:709-721 (1979).

Fluorescence spectra were recorded on a fully corrected photon counting spectrofluorometer Model SLM 8000 DS (SLM-Aminco, Urbana, Ill.) equipped with two red-sensitive, extended $S_{20}$photomultipliers (EMI 9658), and interfaced with a microcomputer system Model 9825 S (Hewlett-Packard, Sunnyvale, Calif.). Tetrapyrrole solutions were monitored at room temperature on 0.3 ml samples, in cylindrical microcells, 3 mm in diameter. Conversion of the digital spectral data into concentrations was performed automatically by the microcomputer, following the recording of the pertinent spectra, according to the method of Rebeiz, C. A. and H. Daniell, and J. R. Matteis, Biotech. Biotech. Bioengi. symp. No. 12:413-439 (1982), in Energy Production and Conservation, Scott, C. D., ed. (John Wiley and Sons, New York, 1982), pp.

The emission and excitation spectra were recorded at excitation and emission bandwidths of 2 mm.

Monovinyl tetrapyrroles were distinguished from divinyl tetrapyrroles by their well-established spectrofluorometric properties in ether at 77° K. (see Rebeiz and Lascelles, supra; Rebeiz, Wu, Kuhadja, Daniell and Perkins, supra; Belanger, F. C., J. X. and C. A. Rebeiz, J. Biol. Chem. 257:1360-1371-(1982); and Belanger, F. C., Duggan, and C. A. Rebeiz, J. Biol. Chem. 257:4849-4858(1982)). The low temperature fluorescence emission and excitation spectra were recorded in cylindrical sample tubes as described in Cohen, C. E. and C. A. Rebeiz, Plant Physiol. 61:824-829 (1978).

Absorption spectra were recorded with an Aminco dual wavelength spectrophotometer model DW-2 (SLM-Aminco, Urbana, Ill.) operated in the split-beam mode, at a slit width of 2 nm.

The acetone-insoluble residue which was left behind after centrifugation of the tissue homogenate was suspended in distilled water with an all glass tissue grinder Total proteins were determined on a small aliquot of the suspension, after delipidation, according to the method of Rebeiz, C. A., P. A. Castelfranco, and A. H. Engelbrecht, Plant Physiol. 40:281-286(1965).

The seedlings with half of their cotyledons still intact were then used for assessing photodynamic damage by light. The seedlings were exposed to daylight in the greenhouse (400 to 5000 ft. candles at noon, depending on cloud cover) and their growth was evaluated over a period of 10 days. In order to secure a permanent record of the growth behavior of the treated plants, the latter were photographed daily (Kodacolor, 400 ASA, Eastman Kodak Co., Rochester, N.Y.) with a Pentax Super Program camera (Helix, Champaign, Ill.) equipped with an SMC Pentax-A 1:1.4 50 mm lens and a digital back that imprinted on each photograph the date or time of day at which the photograph was taken. Percent photodynamic damage was assessed as the percent death of the sprayed tissue, in response to exposure to sunlight For example, if 10 out of 10 sprayed leaves or cotyledons died as a consequence of exposure to daylight, the photodynamic damage was considered to be 100%. If only five out of the ten sprayed leaves or cotyledons had died, the photo-dynamic damage was considered to be only 50%, etc.

The extent of photodynamic damage was related to the amount of accumulated tetrapyrroles by conventional correlation analysis The amounts of tetrapyrrole that accumulated were expressed in nmoles per 100 mg of tissue protein.

The results of these experiments are shown in Table I and in FIG. III.

TABLE I

| Experiment[1] | Treatment | | Various Concentrations of ALA $\Delta$ change[2] after 17 h of dark-incubation in nmol/100 mg protein | | | | Photodynamic damage (%) |
|---|---|---|---|---|---|---|---|
| | mM ALA | g/acre | PChlide | MP(E) | Proto | Total Tetrapyrroles[3] | |
| A | 0(Control) | 0 | 0.00 | 0.00 | 0.00 | 0.00 | 0 |
| | 5 | 131 | 31.77 | −4.44 | −17.33 | 10.00 | 22 |
| | 10 | 262 | 132.76 | −0.50 | −13.07 | 119.19 | 45 |
| | 15 | 393 | 271.29 | 1.23 | −17.33 | 255.19 | 95 |
| | 20 | 524 | 210.60 | −0.75 | −17.33 | 192.52 | 85 |
| | Correlation coefficient | | 0.988 | | | 0.978 | |
| | Level of significance | | 0.1% | | | 0.1% | |
| B | 0(Control) | 0 | 0.00 | 0.00 | 0.00 | 0.00 | 0 |
| | 1 | 26 | 24.95 | −3.08 | −2.81 | 61.12 | 2 |
| | 5 | 131 | 140.82 | −1.69 | −12.41 | 123.72 | 63 |
| | 10 | 262 | 147.82 | 3.83 | 19.58 | 168.23 | 92 |
| | 15 | 393 | 191.22 | 0.78 | −12.41 | 175.03 | 95 |
| | Correlation coefficient | | 0.998 | | | 0.975 | |
| | Level of significance | | 0.1% | | | 0.1% | |

Figure 3:
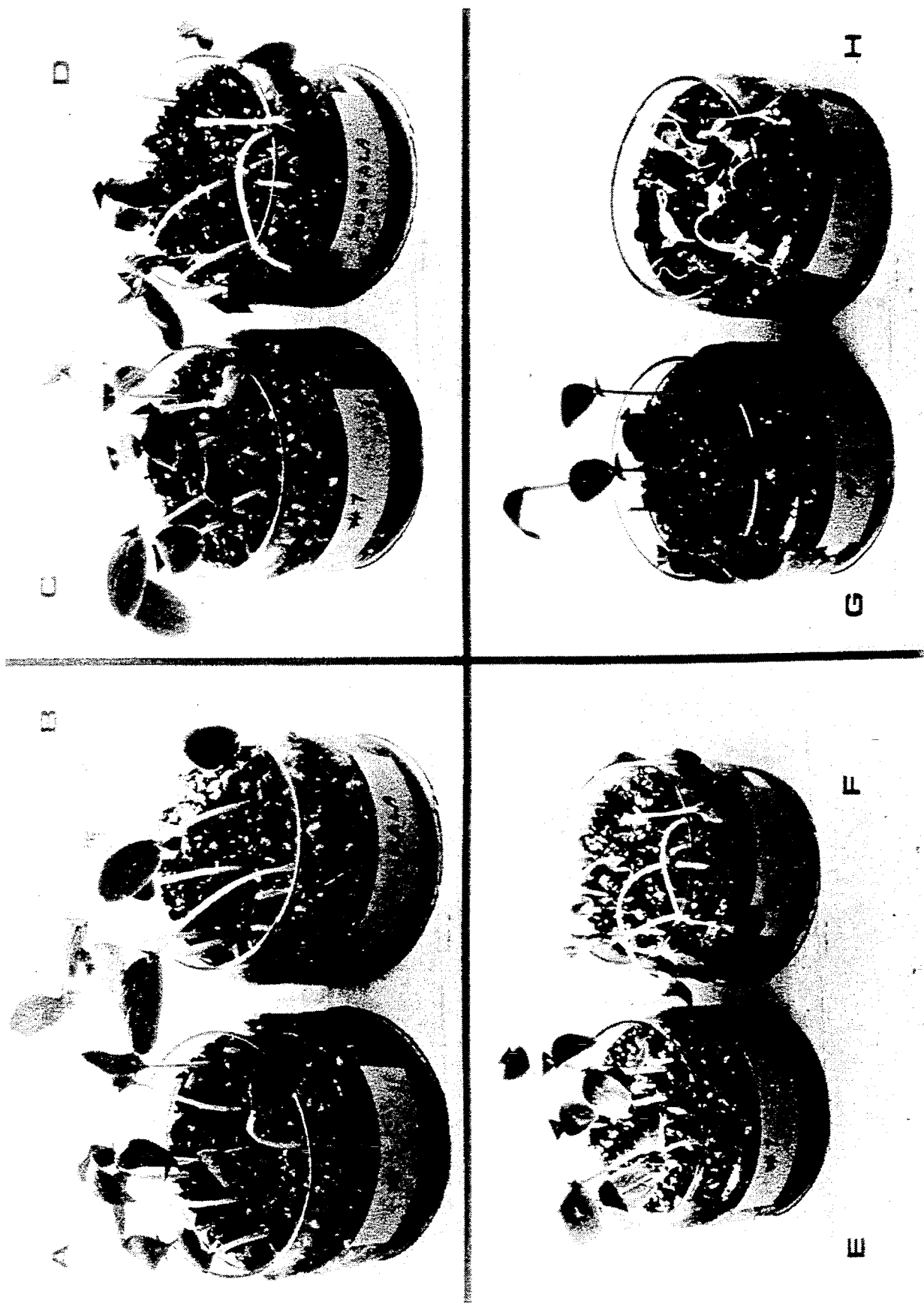
FIG. 3 shows photographs of cucumber seedlings treated with ALA.

[1]In experiment A, the light intensity at noon during the first day of exposure to daylight was about 400 ft. candles. In experiment B, it was about 5000 ft. candles.
[2]The $\Delta$ change in tetrapyrrole concentration is the differences between the tetrapyrrole content of the ALA-treated plants and that of the control plants which were sprayed with the solvent only, i.e. without added ALA, after 17 h of dark incubation and just prior to exposing the plants to daylight. The control plants contained the following amounts of tetrapyrrole after 17 h of dark incubation, and prior to exposure to daylight: A: 99.6, 7.66, 17.33 and B: 22.69, 6.96, and 12.41 nmole PChlide, MP(E) and Proto respectively per 100 mg protein.
[3]= PChlide + MP(E) + Proto FIG. 3 shows the time course of photodynamic damage in 6-day old cucumber seedlings treated with 20 mM (524 g/acre) ALA, followed by a 17-hour dark incubation at 28° C., followed by exposure to daylight in the greenhouse (5000 ft candles at noon). The numbers in the lower right corner of the figures refer either to the time of day or to the date on which the photographs were taken. A,B: control (A) and treated (B) plants immediately after 17 hours of dark-incubation;. C,D: the same control (C) and treated (D) plants after 2 hours of exposure to daylight; E,F: the same control (E) and treated (F) plants after 5 hours of exposure to daylight; G,H: the same control (G) and treated (H) plants after 24 hours in the greenhouse. After 17 hours of dark-incubation the theater plants accumulated 382.82 and 2.36 nmoles of PChlide and MP(E) respectively, per 100 mg protein, above and beyond the controls.

The symptoms of photodynamic damage assumed two forms: bleaching of the green leafy tissue, which spread gradually, e.g. FIG. 3 H; and severe bleaching of the hypocotyl, e.g. FIG. 3 D,F. In both cases, this was accompanied by a severe loss of turgidity of the affected tissues. It is believed that the photodynamic damage, affected the cell membranes which became leaky and this in turn resulted in a rapid and severe dehydration of the tissues. For example, at ALA concentrations of 10–20 mM (262–524 g/acre) a large number of seedlings had undergone irreversible damage after four to five hours of exposure to daylight (FIG. 3 F). The cause of death was usually due to severe dehydration, bleaching, and collapse of the leafy and/or hypocotyl tissues (FIG. 3 F,H). On the other hand, treated samples kept for the same period of time in darkness were unaffected (see Example V).

Example II

Inducers of ALA

In a procedure analogous to that of Example I, the following representative compounds have been found to be effective inducers of ALA:
o-phenanthroline
1,7-phenanthroline
4,7-phenanthroline
phenanthridine Cucumber seedlings were germinated and grown as in Example I. Six-day old green seedlings were thinned to 10 plants per container and sprayed in the late afternoon with 0.25 ml of one of the herbicidal compositions A-P below at the spray rate indicated. Controls were sprayed with solvent only. The solvent was 0.45 acetone:0.45 ethanol:0.1 Tween 80:9 water (v/v/v/v), adjusted to pH 3.5 with HCl. The plants were wrapped in foil overnight, then the next day unwrapped and placed in the greenhouse for 10 days, at which time the photodynamic damage was determined according to the method of Example I.

Figures 1, 4:
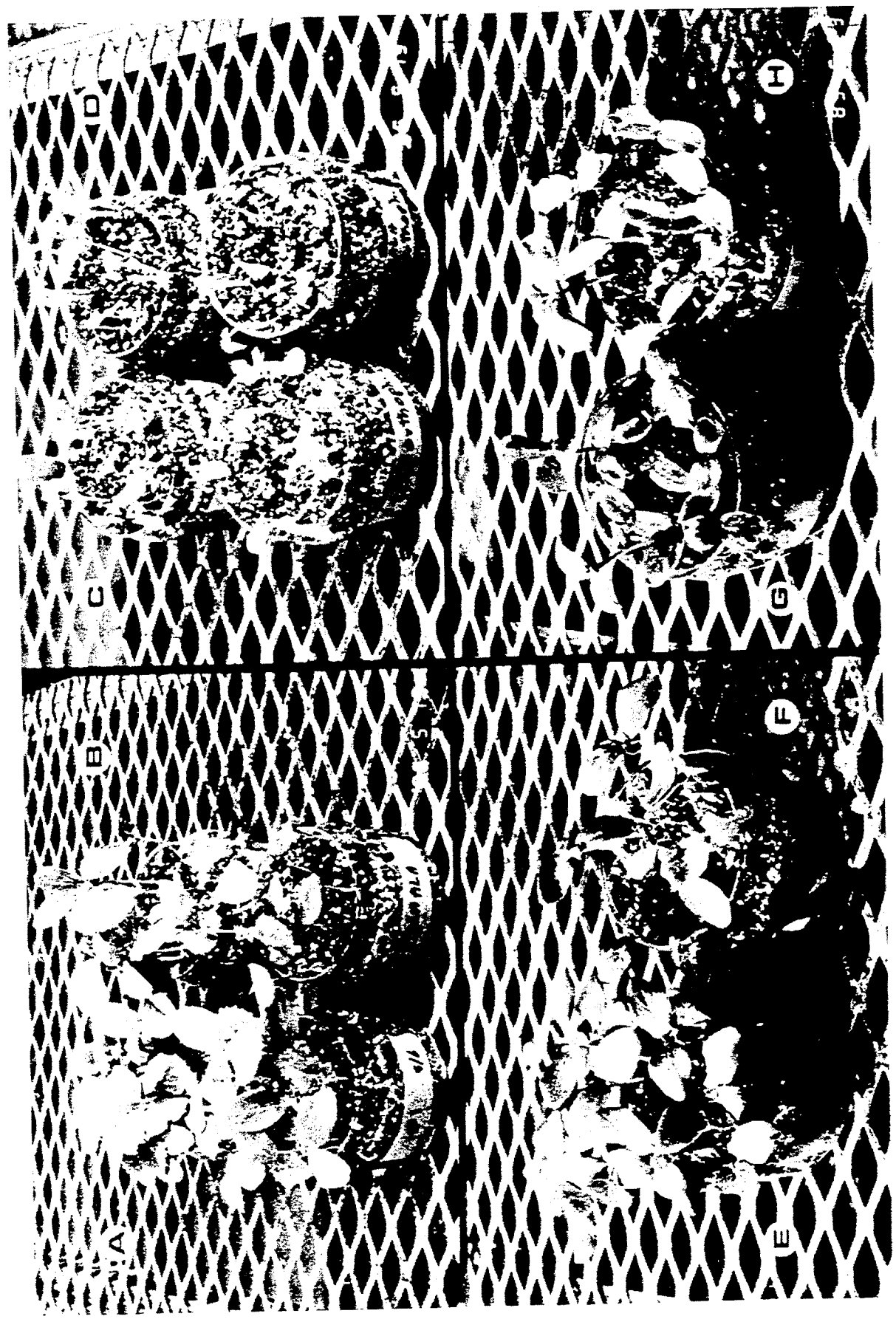
FIG. 4 (FIGS. 4-1 and 4-2) shows photographs of control seedlings and seedlings treated with ALA or with an inducer or with ALA plus an inducer.
Figures 2, 4:
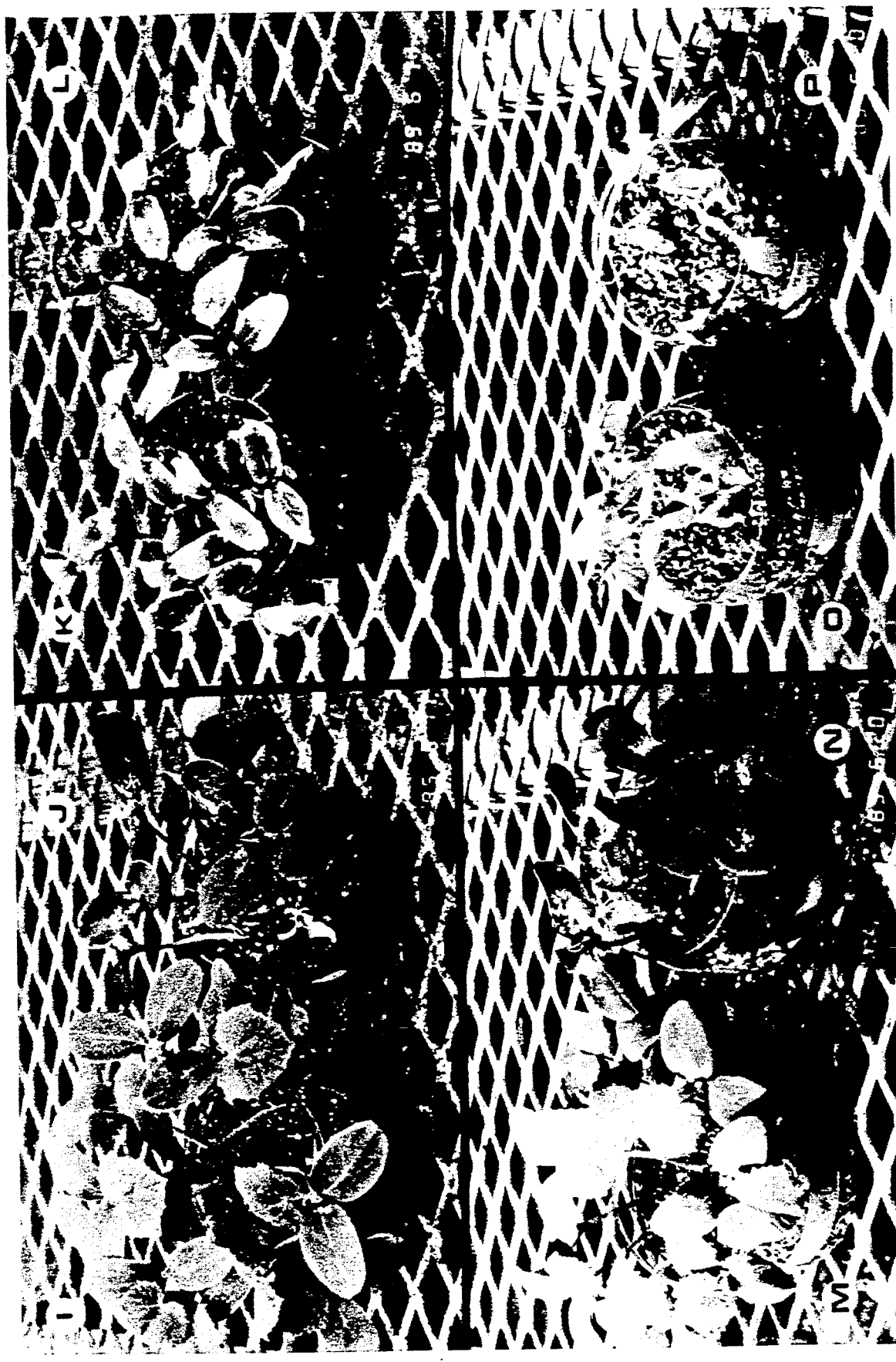

Results are given in Table II and in FIG. 4

TABLE II

| Composition | Treatment (g/acre) | % Photodynamic Damage |
|---|---|---|
| A | Control | 0 |
| B | 131 ALA | 10 |
| C | 849 o-phenanthroline | 97 |
| D | 131 ALA + 849 o-phenanthroline | 100 |
| E | Control | 0 |
| F | 131 ALA | 75 |
| G | 849 1,7-phenanthroline | 85 |
| H | 131 ALA + 849 1,7-phenanthroline | 85 |
| I | Control | 0 |
| J | 131 ALA | 45 |
| K | 849 4,7-phenanthroline | 73 |
| L | 131 ALA + 849 4,7-phenanthroline | 88 |
| M | Control | 0 |
| N | 131 ALA | 55 |
| O | 844 phenanthridine | 83 |
| P | 131 ALA + 844 phenanthridine | 95 |

FIG. 4 shows damage done to treated plants after 5 days.

Example III

Enhancement by 2,2'-DP of ALA-Induced Tetrapyroole Accumulation and Ensuring Photodynamic Herbicidal Damage 2,2'-Dipyridyl (2,2'-DP) is a relatively cheap and easily available chemical. The procedure of Example I was repeated using various mixtures of 2,2'-DP (Sigma Chemical Co., St. Louis, Mo.) and ALA. The results are shown in Tables III, IV, and V:

TABLE III

| | | Various Concentrations of 2,2'-DP | | | | |
|---|---|---|---|---|---|---|
| | | $\Delta$ change[1] after 17 h of dark-incubation in nmol/100 mg protein | | | | |
| Experiment | Treatment[2] | PChlide | MP(E) | Proto | Total Tetrapyrroles[3] | Photodynamic damage (%) |
| A | Control[1] | 0.0 | 0.00 | 0.00 | 0.00 | 0 |
| | 5 mM ALA + 1 mM 2,2'-DP | 54.23 | −0.46 | −7.66 | 46.11 | 40 |
| | 5 mM ALA + 2 mM 2,2'-DP | 107.90 | 0.64 | −1.56 | 106.95 | 62 |
| | 5 mM ALA + 4 mM 2,2'-DP | 170.51 | −0.51 | −12.45 | 157.55 | 90 |
| | Correlation coefficient | 0.99 | | | 0.986 | |
| | Level of significance | 0.1% | | | 0.1% | |
| B | Control | 0.0 | 0.00 | 0.00 | 0.00 | 0 |
| | 5 mM ALA + 1 mM 2,2'-DP | 107.65 | 1.47 | 1.52 | 110.64 | 60 |
| | 5 mM ALA + 2 mM 2,2'-DP | 87.66 | 0.45 | 1.60 | 89.80 | 55 |
| | 5 mM ALA + 4 mM 2,2'-DP | 304.00 | 17.89 | −1.07 | 320.82 | 100 |
| | Correlation coefficient | 0.93 | 0.78 | | 0.93 | |
| | Level of significance | 1% | n.s. | | 1% | |

[1] The $\Delta$ change in tetrapyrrole concentration and the controls are as defined in Table I. The control cucumber seedlings contained the following amounts of tetrapyrroles after 17 h of dark incubation, just prior to exposure to daylight: A: 51.08, 3.28 and 12.45 and B: 21.20, 1.63 and 1.07 nmol PChlide, MP(E) and Proto respectively per 100 mg protein.
[2] In this experiment 5 mM ALA is equivalent to a spray rate of 131 g/acre, and 1, 2, and 4 mM 2,2'-DP are equivalent to spray rates of 27, 54, and 107 g/acre respectively.
[3] = PChlide + MP(E) + Proto

TABLE IV

| | | Various Concentrations of ALA in the Presence of Increasing Amounts of 2,2'-DP | | | | |
|---|---|---|---|---|---|---|
| | | $\Delta$ change[1] after 17 h of dark-incubation in nmol/100 mg protein | | | | |
| Experiment | Treatment[2] | PChlide | MP(E) | Proto | Total Tetrapyrroles[3] | Photodynamic damage (%) |
| A | Control[1] | 0.00 | 0.00 | 0.00 | 0.00 | 0 |
| | 5 mM 2,2'-DP + 1 mM ALA | 47.36 | 8.47 | −1.18 | 54.65 | 10 |
| | 5 mM 2,2'-DP + 3 mM ALA | 109.89 | 7.64 | −2.55 | 114.98 | 55 |
| | 5 mM 2,2'-DP + 5 mM ALA | 138.75 | 4.20 | −2.55 | 140.40 | 95 |
| | Correlation coefficient | 0.96 | 0.18 | | 0.944 | |
| | Level of significance | 0.1% | n.s. | | 1% | |
| B | Control | 0.00 | 0.00 | 0.00 | 0.00 | 0 |
| | 10 mM 2,2'-DP + 1 mM ALA | 136.53 | 28.61 | 0.00 | 165.14 | 40 |

TABLE IV-continued

Various Concentrations of ALA in the Presence of Increasing Amounts of 2,2'-DP

| Experiment | Treatment[2] | Δ change[1] after 17 h of dark-incubation in nmol/100 mg protein | | | | Photodynamic damage (%) |
|---|---|---|---|---|---|---|
| | | PChlide | MP(E) | Proto | Total Tetrapyrroles[3] | |
| | 10 mM 2,2'-DP + 3 mM ALA | 182.10 | 66.35 | 0.00 | 248.45 | 65 |
| | 10 mM 2,2'-DP + 5 mM ALA | 284.4 | 141.60 | 0.00 | 426.00 | 95 |
| | Correlation coefficient | 0.995 | 0.957 | | 0.994 | |
| | Level of significance | 0.1% | 0.1% | | 0.1% | |
| C | Control | 0.00 | 0.00 | 0.00 | 0.00 | 0 |
| | 15 mM 2,2'-DP + 1 mM ALA | 99.41 | 60.87 | 1.47 | 161.75 | 10 |
| | 15 mM 2,2'-DP + 3 mM ALA | 171.56 | 101.86 | 25.63 | 299.05 | 95 |
| | 15 mM 2,2'-DP + 5 mM ALA | 277.06 | 141.37 | 5.91 | 424.34 | 100 |
| | Correlation coefficient | 0.90 | 0.90 | 0.7 | 0.92 | |
| | Level of significance | 1% | 1% | n.s. | 1% | |

[1]The Δ change in tetrapyrrole content and the controls are as defined in Table I. The control cucumber seedlings contained the following amounts of tetrapyrroles just prior to exposure to daylight: A: 20.24, 2:51, 2.55; B: 36.1, 0.57, 0.00; C: 21.81, 0.82, 0.74 nmoles PChlide, MP(E), and Proto respectively per 100 mg protein.
[2]In this experiment, 5, 10, and 15 mM 2,2'-DP are equivalent to a spray rate of 134, 268, and 402 g/acre respectively, and 1, 3, and 5 mM ALA are equivalent to a spray rate of 26, 78, and 131 g/acre, respectively.
[3]= PChlide + MP(E) + Proto

TABLE V

ALA + 2,2'-DP
Dimethyl Sulfoxide (DMSO)

| Treatment[2] | Δ Change[1] after 17 h of dark-incubation in nmol/100 mg protein | | | | % Photo-dynamic Damage |
|---|---|---|---|---|---|
| | PChlide | MP(E) | Proto | Total Tetra-pyrroles[3] | |
| Control[1] | 0.00 | 0.00 | 0.00 | 0 | 0 |
| Control + 15 mM DMSO | 12.9 | 0.57 | 0.00 | 13.47 | 0 |
| 5 mM ALA | 83.41 | 0.96 | 0.00 | 84.37 | 30 |
| 5 mM ALA + 15 mM DMSO | 15.75 | 0.11 | 0.00 | 15.86 | 5 |
| 15 mM 2,2'-DP | 6.73 | 11.67 | 2.63 | 21.03 | 10 |
| 15 mM 2,2'-DP + 15 mM DMSO | 9.64 | 0.03 | 1.53 | 11.20 | 5 |
| 5 mM ALA + 15 mM 2,2'-DP | 64.88 | 25.70 | 8.11 | 98.69 | 80 |
| 5 mM ALA + 15 mM 2,2'-DP + 15 mM DMSO | 34.40 | 0.05 | 2.75 | 37.20 | 10 |
| Correlation coefficient | 0.742 | 0.86 | 0.85 | 0.901 | |
| Level of Significance | 5% | 1% | 1% | 1% | |

[1]The Δ change in tetrapyrrole content and the control are as defined in Table I. The control cucumber seedlings contained the following amounts of tetrapyrroles just prior to exposure to daylight: 17.34, 0.56 and 0.00 nmol PChlide, MP(E) and Proto respectively per 100 mg plastid protein.
[2]In this experiment, 15 mM DMSO is equivalent to a spray rate of 184 g/acre; 5 mM ALA is equivalent to a spray rate of 131 g/acre, and 15 mM d,d'-DP is equivalent to a spray rate of 402 g/acre.
[3]= PChlide + MP(E) + Proto The results demonstrate that in the presence of low amounts of ALA (5 mM, 131 g/acre), increasing amounts of 2,2'-DP (1, 2, or 4 mM=27, 54, or 107 g/acre, respectively) enhanced significantly the tetrapyrrole biosynthetic capabilities of the treated tissues; it also enhanced the photodynamic herbicidal properties of the mixtures (Table III). In the presence of various amounts of 2,2'-DP, ranging from 5–10 mM (134–268 g/acre), increasing amounts of ALA (1–5 mM, 26–131 g/acre) also resulted in increased tetrapyrrole accumulation and in enhanced photodynamic herbicidal activity of the mixtures up to a concentration of 5 mM ALA (131 g/acre) (Table IV A, B). Further increases in the amount of added 2,2'-DP appeared to enhance the photodynamic herbicidal effectiveness of the ALA+2,2'-DP treatment only at very low ALA concentrations (i.e., 3 mM, 78 g/acre)(Table IV C). ALA and 2,2'-DP appeared to act synergistically to produce photodynamic damage (Table V). The addition of 15 mM (184 g/acre) dimethyl sulfoxide (a penetration enhancer) to the ALA+2,2'-DP mixture was inhibitory and did not appear to enhance the effectiveness of the spray (Table V).

Example IV

Enhancers of ALA Conversion to Photodynamic Tetrapyrroles

As described above, 2,2'-DP is preferred as an enhancer of ALA. However, in a procedure analogous to that of Example I, the following representative compounds have also been found to be effective enhancers, producing a synergistic effect in combination with ALA:

2,3'-DP
4,4'-DP
picolinic acid
pyridine aldehyde
a pyridine aldoxime

Cucumber seedlings were germinated and grown as in Example I. Six-day old green seedlings were thinned to 10 plants per container and sprayed in the late afternoon with 0.25 ml of one of the herbicidal compositions A-FF below at the spray rate indicated. Controls were sprayed with solvent only. The solvent was 0.45 acetone:0.45 ethanol:0.1 Tween 80:9 water (v/v/v/v), adjusted to pH 3.5 with HCl. The plants were wrapped in foil overnight, then the next day unwrapped and placed in the greenhouse for 10 days, at which time the % photodynamic damage was determined according to the method of Example I.

Figures 1, 5:
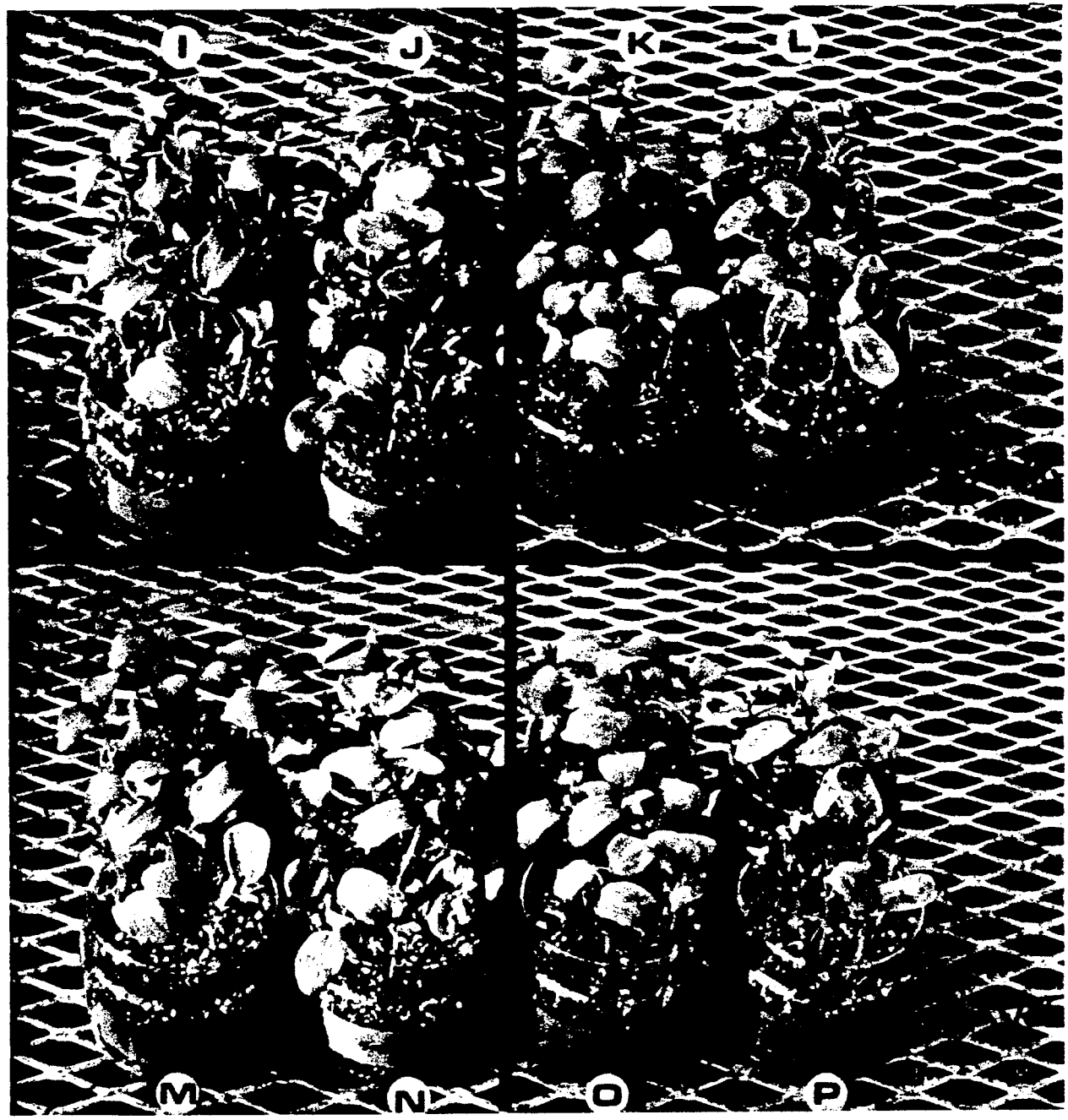
FIG. 5 (FIGS. 5-1 and 5-2) shows photographs of control cucumber seedlings and seedlings treated with ALA or with an enhancer or with ALA plus an enhancer.
Figures 2, 5:

Results are shown in Table VI and in FIG. 5:

TABLE VI

Enhancers of ALA

| Composition | Treatment (g/acre) | % Photodynamic Damage |
|---|---|---|
| A | Control | 0 |
| B | 131 ALA | 75 |
| C | 526 2,3'-DP | 0 |
| D | 131 ALA + 526 2,3'-DP | 85 |
| E | Control | 0 |
| F | 131 ALA | 83 |
| G | 789 2,4'-DP | 0 |
| H | 131 ALA + 789 2,4'-DP | 18 |
| I | Control | 0 |
| J | 131 ALA | 20 |
| K | 789 4,4'-DP | 0 |
| L | 131 ALA + 789 4,4'-DP | 25 |

TABLE VI-continued
Enhancers of ALA

| Composition | Treatment (g/acre) | % Photodynamic Damage |
|---|---|---|
| M | Control | 0 |
| N | 131 ALA | 20 |
| O | 537 4,4'-DP | 0 |
| P | 131 ALA + 537 4,4'-DP | 75 |
| Q | Control | 0 |
| R | 131 ALA | 85 |
| S | 684 8-hydroxyquinoline | 0 |
| T | 131 ALA + 684 8-hydroxyquinoline | 58 |
| U | Control | 0 |
| V | 131 ALA | 43 |
| W | 580 picolinic acid | 3 |
| X | 131 ALA + 580 picolinic acid | 93 |
| Y | Control | 0 |
| Z | 131 ALA | 35 |
| AA | 504 pyridine aldehyde | 0 |
| BB | 131 ALA + 504 pyridine aldehyde | 93 |
| CC | Control | 0 |
| DD | 131 ALA | 20 |
| EE | 575 pyridine aldoxime | 0 |
| FF | 131 ALA + 575 pyridine aldoxime | 58 |

FIG. 5 depicts experiments I-P and U-BB 5 days after treatment.

Example V

Light Requirement

Six-day old green cucumber seedlings were sprayed according to the procedure of Example I with high concentrations (20 mM each) of ALA and 2,2'-DP solutions, after which the treated plants and the controls (which were sprayed with the solvent only) were incubated in the dark for 17 hours in order to induce the accumulation of tetrapyrroles. The next morning, the control and treated plants were photographed under cool white fluorescent light and under ultraviolet (360 nm) light, in the latter case in order to detect visually the accumulated tetrapyrroles by their red fluorescence. The photographed plants were then exposed to daylight (about 4500 ft. candles) in the greenhouse in order to elicit photodynamic damage. Duplicate sets of treated and control plants were kept in darkness for an equal length of time, in order to determine whether the accumulation of massive amounts of tetrapyrrole causes damage in darkness. After 6 hours of exposure to daylight or to darkness, the treated and control plants were compared (FIG. 6).

Figure 6:
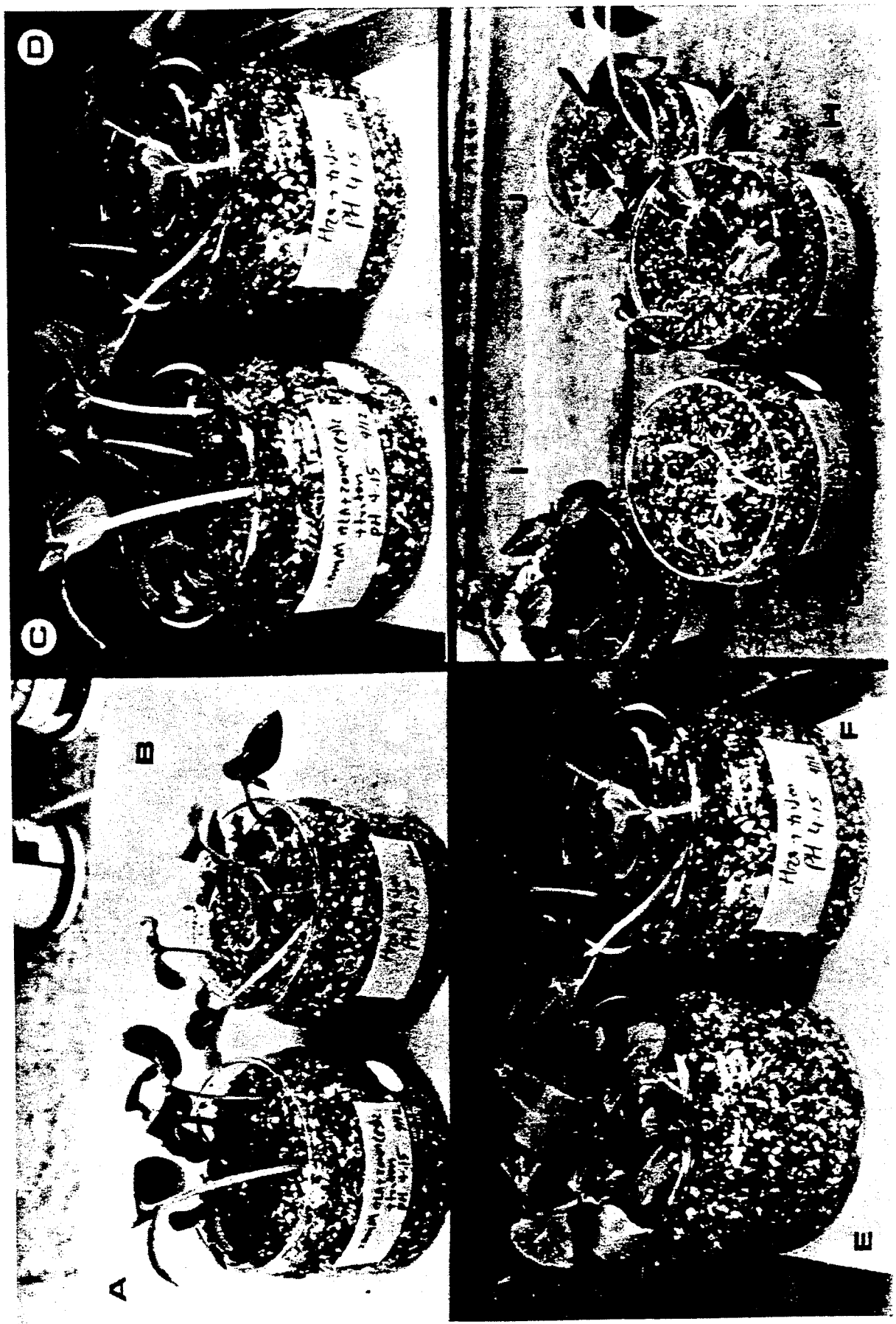
FIG. 6 shows photographs demonstrating the effect of light in addition to tetrapyrrole accumulation for the occurence of photodynamic damage.
Figure 7:
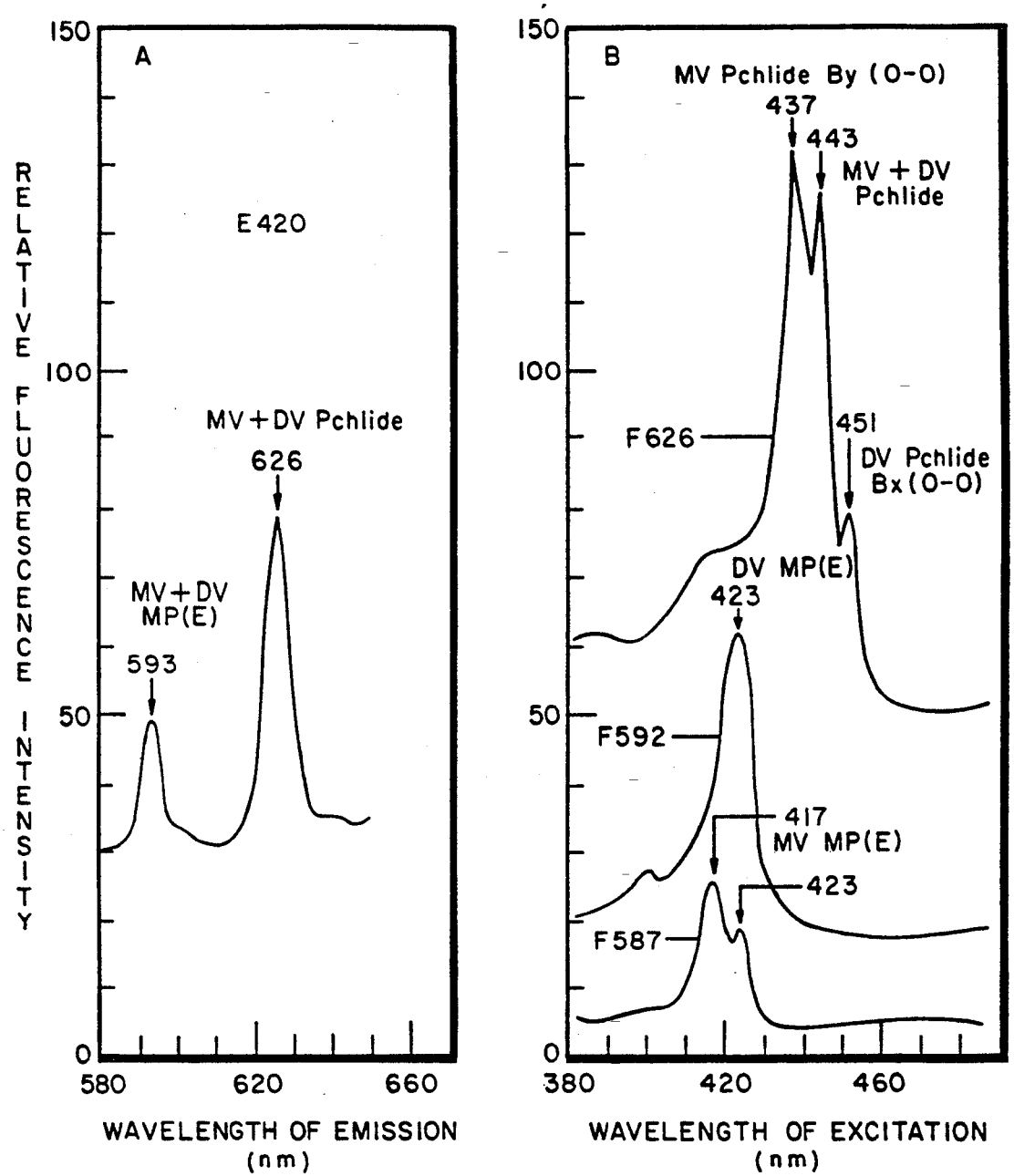
FIG. 7 shows the fluorescence emission (A) and excitation (B) spectra in ether at 77° K. of MP(E)+PChlide pools of cucumber seedlings treated with ALA+enhancer, and placed in darkness.

FIG. 6 shows the requirement of light in addition to tetrapyrrole accumulation for the occurence of photodynamic damage. A,B: treated (A) and control (B) plants immediately after 17 hours of dark incubation; C,D: the same treated (C) and control (D) plants viewed under 360 nm ultraviolet light, in order to show the accumulation of red-fluorescing tetrapyrroles in the stems of the treated seedlings; E,F: the same treated (E) and control (F) plants photographed from another angle to show the accumulation of red-fluorescing tetrapyrroles in the stems, the growing points and leafy parts of the treated seedlings; G,H: the same treated (G) and control (H) plants after about 6 hours of exposure to daylight; I,J: treated (I) and control (J) plants left in darkness for 6 hours while plants G,H were being exposed to daylight. The induction of massive tetrapyrrole accumulation in the ALA+2,2'-DP treated plants, but not in the controls, is depicted pictorially in FIG. VI C, D, E, F. Only the ALA+2,2'-DP treated plants exhibited red-tetrapyrrole fluorescence in the stems and in the leafy tissues (FIG. 6 C, E). After 6 hours of exposure to daylight, the ALA+2,2'-DP, treated plants were completely destroyed (FIG. 6 G) while the control plants grew normally (FIG. 6 H). Finally, the duplicate controls and ALA+2,2'-DP treated plants which were kept for 6 hours in darkness remained green and healthy (FIG. VI I, J).

These results clearly indicate that the ALA+2,2'-DP treatment caused photodynamic damage only in the presence of light, and demonstrates the correlation between damage and accumulated tetrapyrroles.

Example VI

Fluorescence Emission and Excitation Spectra

FIG. VII describes fluorescence emission (A) and excitation (B) spectra in ether at 77° K. of the MP(E) +PChlide pools of 6-day old cucumber seedlings treated with 0.25 ml of 5 mM ALA+15 mM 2,2'-DP, and placed in darkness at 28° C. for 17 hours. The MP(E)+PChlide pools were extracted and transferred to ether, immediately after incubation as described in Example I. The emission spectrum, showing MV+DV MP(E) emission at 593 nm and MV+DV PChlide emission at 626 nm was elicited by excitation at 420 nm. The excitation spectra showing MV and DV MP(E) maxima at 417 and 423 nm respectively as well as MV [By(0-0)-] and DV [Bx(0-0)] PChlide maxima at 437 and 451 nm respectively, were recorded at the indicated emission maxima (i.e., F-values shown in FIG. VII). The spectrofluorometric properties of these pools are described in detail in the two papers by Belanger and Rebeiz, supra, and by Belanger, Duggan, and Rebeiz, supra. Baselines were arbitrarily adjusted along the ordinate axis in order to avoid overlap of the spectra. Arrows point to the wavelength maxima of the indicated pools.

Example VII

Relationship Between the Accumulated Tetrapyrroles and the Incidence of Photodynamic Damage The correlation between ALA+2,2'-DP induced tetrapyrrole accumulation and photodynamic damage was in general significant at the 1% to 0.1% level of significance (Tables I, III-V); the best correlation was observed between PChlide accumulation and photodynamic damage. A significant correlation between MP(E) and Proto accumulation and photodynamic damage was observed only after their concentration had reached a certain threshold concentration (Tables I, III vs. IV, V).

Figure 8:
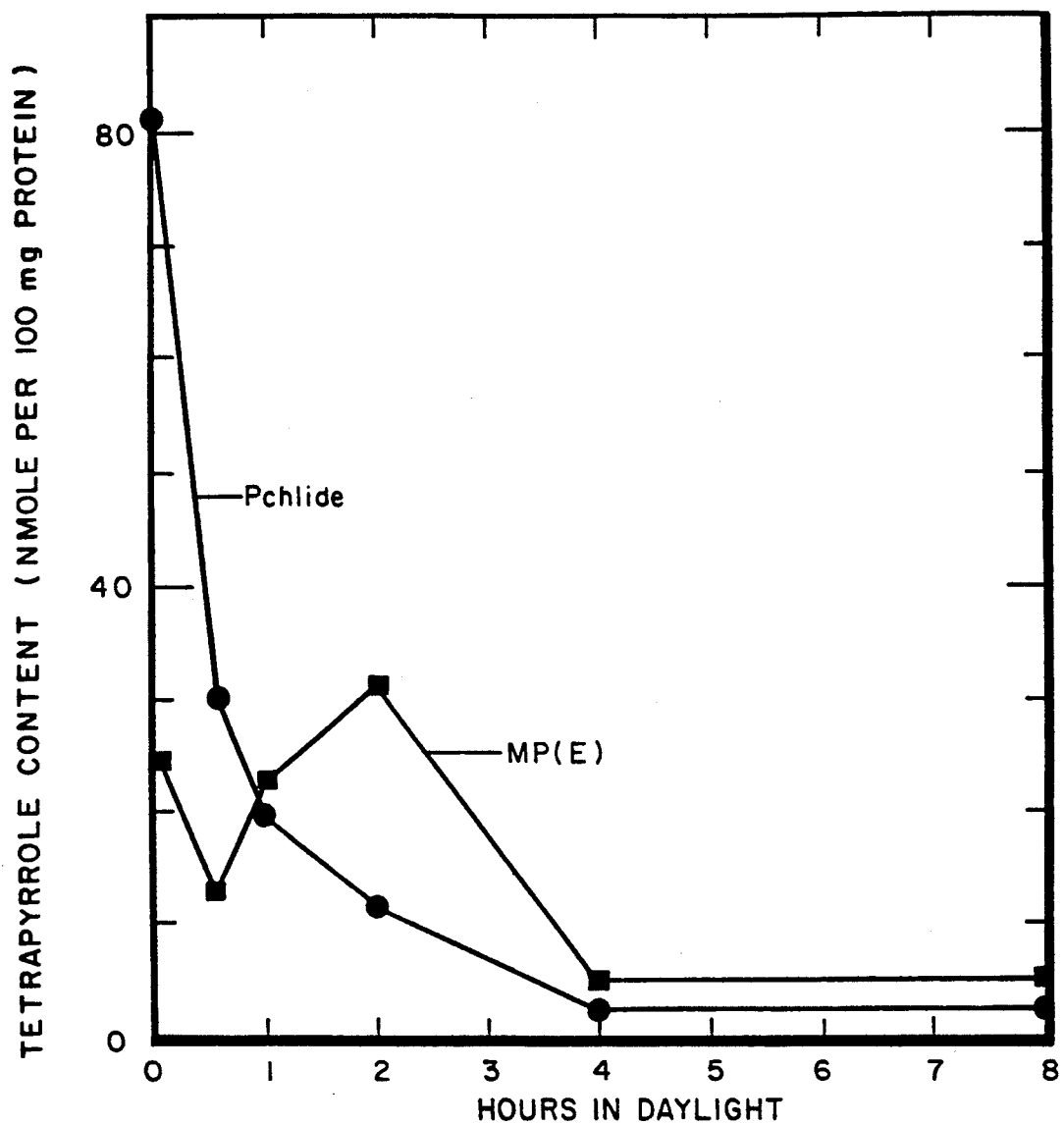
FIG. 8 shows the time course of PChlide and MP(E) disappearance in daylight.

As depicted in FIG. VII, significant amounts of both MV and DV PChlide and MP(E) accumulate in ALA+2,2'-DP treated plants. FIG. 8 shows the time course of PChlide and MP(E) disappearance in daylight In a manner analogous to Example I, 6-day old cucumber seedlings were treated with 0.25 ml of 5 mM ALA+15 mM 2,2'-DP, pH 3.5. They were then placed in darkness at 28° C. for 17 hours. They were analyzed for tetrapyrrole content at the end of the 17 hour dark incubation and after the indicated times of exposure to daylight (~3000 ft. candles at noon). Negligible amounts of Proto were formed during dark incubation. In this particular experiment the average photodynamic damage of six replicates amounted to 80%. After 8 hours of exposure to daylight in the greenhouse and after a brief transient rise in MP(E) content, 76% and 93% of the MP(E) and PChlide pools, respectively, had disappeared, probably as a consequence of photodestruction. It is known that ALA-induced PChlide is destroyed and not converted to Chl under high light intensities such as the ones (4000 to 6000 ft. candles) which are encountered on a typical clear day in the greenhouse; see, e.g., Sisler, E. C., and W. H. Klein, Physiol. Plant. 16:315–322(1963).

Example VIII

Post-Spray Dark Period

Six-day old cucumber seedlings were sprayed according to the procedure of Example I with 0.25 ml of solvent (controls) or with solvent containing 5 mM ALA+indicated concentrations of 2,2'-DP at pH 3.5, and were placed overnight in darkness at 28° C. The next morning, i.e. after 17 hours of dark-incubation, the control and treated plants were exposed to daylight. At the same time, similar greenhouse-grown seedlings of the same age were likewise sprayed with solvent only (controls) or with ALA+2,2'-DP (treated) and were exposed to daylight in the greenhouse without an intervening dark-incubation period. The results of this experiment are depicted in Table VII:

TABLE VII

Post-Spray Dark-Incubation Period

| Experiment | Treatment[3] | Photodynamic damage % |
|---|---|---|
| A[1] | Control with post-spray dark-incubation | 0 |
| | 5 mM ALA + 15 mM 2,2'-DP with post-spray dark-incubation | 83 |
| | Control without post-spray dark-incubation | 0 |
| | 5 mM ALA + 15 mM 2,2'-DP without post-spray dark-incubation | 27 |
| B[2] | Control without post-spray dark-incubation | 0 |
| | 5 mM ALA + 15 mM 2,2'-DP without post-spray dark-incubation | 22 |
| C[2] | Control without post-spray dark-incubation | 0 |
| | 5 mM ALA + 5 mM 2,2'-DP without post-spray dark-incubation | 12 |

[1]A: 7-day-old green cucumber seedlings were sprayed with 0.25 ml of solvent (control) or with 0.25 ml of solvent containing 5 mM ALA + 15 mM 2,2'-DP, pH 3.5. The next day, after 17 h of dark-incubation, the control and treated plants were exposed to daylight. At the same time, cucumber seedlings of the same age were sprayed with 0.25 ml of solvent (control) or with the solvent containing ALA + 2,2'-DP and were placed immediately in daylight without an intervening dark-incubation period.
[2]B,C: 6-day-old green cucumber seedlings were sprayed with 0.25 ml of solvent or with the solvent containing 5 mM ALA and 15 mM 2,2'-DP and were placed immediately in daylight without an intervening dark-incubation period.
[3]In this experiment, 5 mM ALA is equivalent to a spray rate of 131 g/acre; 5 and 15 mM 2,2'-DP are equivalent to spray rates of 134 and 402 g/acre respectively.

It is evident from Table VII that a post-spray dark incubation period is recommended for the full expression of the ALA+2,2'-DP photodynamic herbicidal activity in solvent systems such as the ones used in this experiment. Treated plants that were subjected to a post-spray dark-incubation exhibited about 3-fold more photodynamic damage than treated plants that were not subjected to a post-spray dark-incubation period.

Example IX

Photodynamic Herbicidal Response of Various Plant Species to ALA+2,2'-DP Treatment The procedure of Example I was performed on the following representative monocots and dicots:
Cucumber (*Cucumis sativus* L. cv Beit Alpha MR)
Lambsquarter (*Chenopodium album*)
Mustard (*Brassica kaber/juncea*)
Red root pigweed (*Amaranthus retroflexus*)
Common purslane (*Portulaca oleracea*)
Tomato (*Lycopersicon esculentum* cv Jet Star)
Cotton (*Gossypium herbacium* cv Coker-315)
Red kidney bean (*Phaseolus vulgaris* L. cv California Dark Red)
Soybean (*Glycine max* cv Williams)
Perennial bluegrass (*Poa pratensis* cv Aspen)
Barley (*Hordeum vulgare*, var. Beacon Spring)
Sweet corn (*Zea mays* L. cv Gold Cup)
Crabgrass (*Digitaria sanguinalis* L. and *Digitaria ischaemum*)
Giant foxtail (*Setaria faberii*)
Oat (*Avena sativa* cv Centennial)
Wheat (*Triticum sativum* cv Auburn)

The greenhouse-grown seedlings were treated with 0.25 ml of 5 mM (131 g/acre) ALA+15 mM (402 g/acre) 2,2'-DP, pH 3.5. Controls were treated with solvent only. All plants were then incubated in the dark for 17 hours. The next morning the seedlings were sampled in the dark for tetrapyrrole content using the procedure of Example I for dicots and the following procedure for monocots the seedlings of one of the two replicates were excised into an upper half and a lower half. The two batches of excised tissue were then homogenized separately in a Sorval Omnimixer in acetone:0.1N NH$_4$OH (9:1 v/v) at a rate of 18 ml of solvent per 3 g of tissue. The other replicate was used to assess the photodynamic effect of light on the seedlings. For some dicots, the stems as well as the leaves were analysed for tetrapyrroles. The results are given in Table VIII:

TABLE VIII

Photodynamic Herbicidal Response of Various Plant Species to ALA + 2,2'-DP Spray

| Plant | Age at spraying (days) | Type of herbicidal response[1] | PChlide Control | PChlide Treated | MP(E) Control | MP(E) Treated | Proto Control | Proto Treated | Photodynamic damage (%) Control | Photodynamic damage (%) Treated |
|---|---|---|---|---|---|---|---|---|---|---|
| Cucumber cotyledons | 6 | I | 84.79 | 434.12 | 8.51 | 68.85 | 3.64 | 19.06 | 0 | 85 |
| Cucumber stems | 6 | I | 10.87 | 71.77 | 5.32 | 14.47 | 12.67 | 39.37 | 0 | 85 |
| Lambsquarter | 7 | I | 23.52 | 72.58 | 3.83 | 33.94 | 17.59 | 13.87 | 0 | 100 |
| Mustard leaves | 12 | I | 29.84 | 200.82 | 12.01 | 36.11 | 29.08 | 23.52 | 0 | 90 |
| Mustard stems | 12 | I | 15.26 | 49.60 | 2.95 | 13.13 | 0.00 | 38.35 | 0 | |
| Red root pigweed | 11 | I | 29.47 | 59.08 | 1.64 | 20.59 | 0.00 | 2.90 | 0 | 95 |
| Common purslane | 21 | I | 8.37 | 33.30 | 1.54 | 11.79 | 1.88 | 5.71 | 0 | 80 |
| Tomato cotyledons | 13 | I | 27.19 | 114.86 | 0.69 | 34.40 | 0.31 | 0.31 | 0 | 90 |
| Tomato stems | 13 | I | 3.69 | 14.26 | 0.82 | 2.53 | 0.00 | 0.00 | 0 | 90 |
| Cotton cotyledons | 14 | II | 18.06 | 36.53 | 3.95 | 9.22 | 0.00 | 0.00 | 0 | 63 |
| Cotton stems | 14 | II | 3.70 | 4.18 | 1.19 | 1.13 | 0.00 | 0.00 | 0 | 0 |
| Kidney bean leaves | 9 | II | 117.03 | 438.79 | 3.11 | 430.12 | 4.88 | 21.42 | 0 | 100 |
| Kidney bean stems | 9 | II | 36.78 | 82.26 | 3.89 | 75.90 | 3.49 | 14.26 | 0 | 0 |
| Soybean leaves | 9 | II | 25.31 | 98.88 | 3.61 | 105.84 | 4.24 | 10.87 | 0 | 78 |
| Soybean stems | 9 | II | 6.06 | 6.17 | 0.37 | 0.45 | 0.00 | 0.45 | 0 | 0 |
| Perennial bluegrass | 18 | II | 9.87 | 39.46 | 0.39 | 43.52 | 0.54 | 51.46 | 0 | 30–40 |
| Barley | 6 | III | 12.69 | 58.64 | 0.8 | 3.39 | 0.39 | 1.11 | 0 | S.N.[2] |

TABLE VIII-continued

Photodynamic Herbicidal Response of Various Plant Species to ALA + 2,2'-DP Spray

| Plant | Age at spraying (days) | Type of herbicidal response[1] | nmol/100 mg protein | | | | | | Photodynamic damage (%) | |
|---|---|---|---|---|---|---|---|---|---|---|
| | | | PChlide | | MP(E) | | Proto | | | |
| | | | Control | Treated | Control | Treated | Control | Treated | Control | Treated |
| Corn | 9 | III | 79.09 | 85.44 | 4.90 | 15.47 | 12.39 | 0.00 | 0 | S.N. |
| Crabgrass | 25 | III | 44.43 | 114.32 | 3.13 | 27.63 | 0.00 | 0.00 | 0 | S.N. |
| Giant foxtail | 6 | III | 7.87 | 78.75 | 0.44 | 11.91 | 0.00 | 13.92 | 0 | S.N. |
| Oat upper half | 7 | III | 29.19 | 171.96 | 13.02 | 23.04 | 0.00 | 0.00 | 0 | S.N. |
| Oat lower half | 7 | III | 92.53 | 121.86 | 9.37 | 3.84 | 0.00 | 0.00 | 0 | 0.0 |
| Wheat upper half | 7 | III | 29.58 | 101.25 | 8.34 | 5.22 | 9.96 | 0.60 | 0 | S.N. |
| Wheat lower half | 7 | III | 31.87 | 47.23 | 2.10 | 0.99 | 0.00 | 0.00 | 0 | 0.0 |

[1]These types of photodynamic response are discussed below.
[2]S.N. = small necrotic areas.

An examination of the results of this limited survey revealed that plants reacted in three different ways to the ALA+2,2'-DP spray. One group of dicots, which is exemplified by cucumber (FIGS. 3, 4) exhibited what is referred to as Type I herbicidal response in Table VIII. This group of plants reacted to the ALA+2,2'-DP spray exactly as did cucumber. Leafy tissues, stems and growing points accumulated significant amounts of tetrapyrroles and were subject to severe photodynamic damage (Table VIII). Usually, the seedlings died very rapidly, and the rapidity of the response depended on the light intensity in the greenhouse. For example, at the low spray concentrations used in this work (131 g/acre ALA+402 g/acre 2,2'-DP), only 4 to 5 hours of exposure to daylight was sufficient to cause the death of the plants on clear, bright days (4000 to 6000 ft. candles at noon). On the other hand, 2 to 3 days of insolation were required on very cloudy days (400 ft. candles at noon) in order to achieve the same results. Some of the plant species that exhibited this type of photodynamic herbicidal response such as lambsquarter, mustard, redroot pigweed and common purslane are considered to be serious weeds. While 13-day old tomato plants, with fully expanded cotyledons and with small developing primary leaves exhibited a Type I response (Table VIII), younger 8- to 10-day old tomato seedlings were much less affected by the spray (~40% photodynamic damage).

Figure 9:
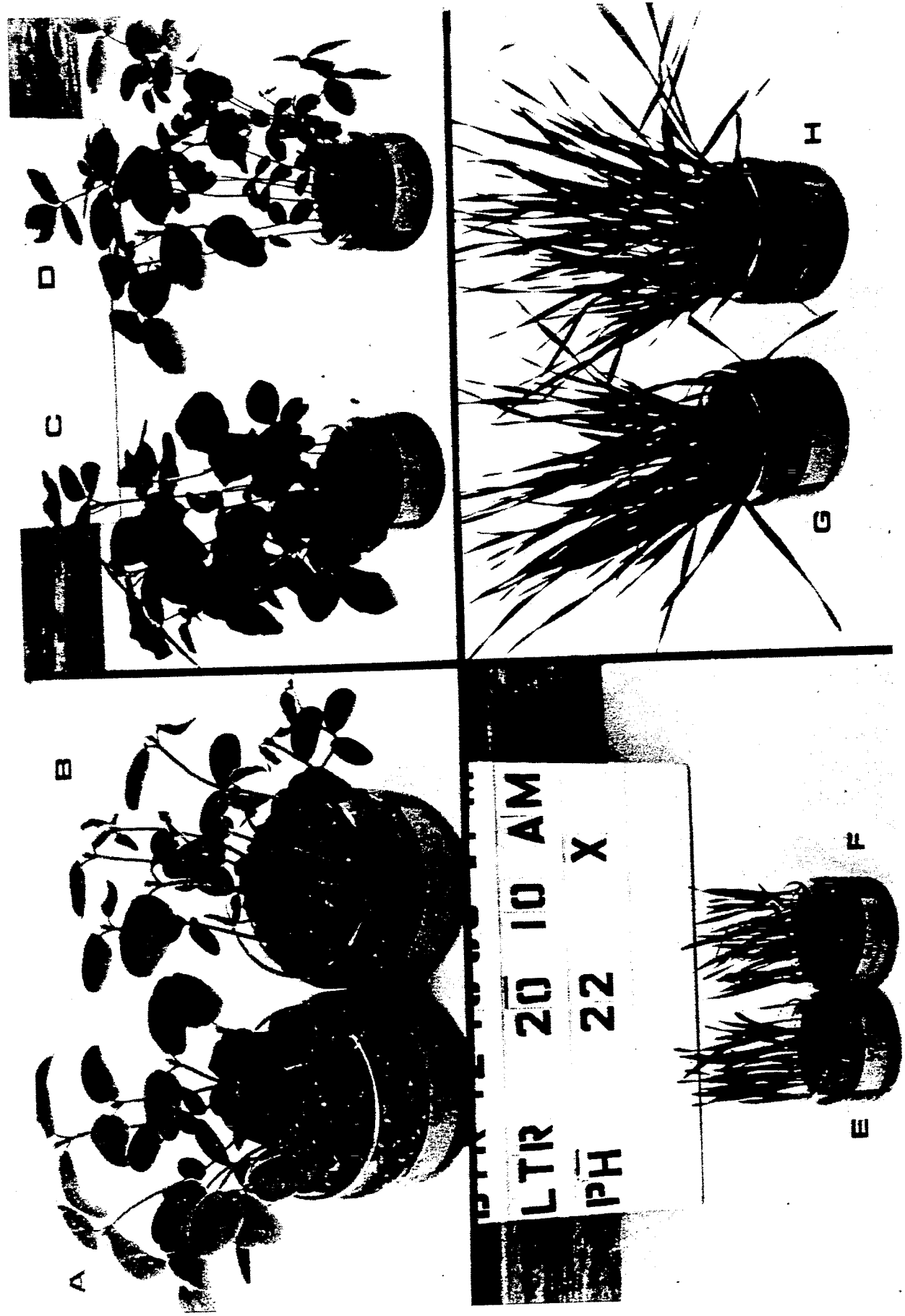
FIG. 9 shows photographs depicting Type II and Type III photodynamic herbicidal response of soybean and barley, and control plants.

Other dicots such as cotton, kidney bean and soybean exhibited a different response to the ALA+2,2'-DP treatment. This response is referred to as Type II in Table VIII. Plants belonging to this group accumulate significant amounts of tetrapyrroles in the leafy tissues, but not in the stems as in cotton and soybean. Other species such as kidney bean also accumulated some tetrapyrroles in the stems. Leaves that accumulate tetrapyrroles exhibit very severe photodynamic damage and die within a few hours (FIG. 9). However, the cotyledons, stems, and growing points remain unaffected. Such plants usually recovered from the original photodynamic damage by producing new leaves (FIG. 9) and may require a second application. In this group the Type II response also depended on the age of the seedlings. For example, 6-day old soybean in which the primary leaves were still enclosed within the cotyledons were completely unaffected by the ALA+2,2'-DP treatment. On the other hand, 9-day old soybean plants, with expanded primary leaves, exhibited a typical Type II photodynamic herbicidal response (FIG. IX B). The only monitored monocot that exhibited this type of response was perennial blue grass in which about 30-40% of the sprayed leaves died; the plants subsequently recovered and developed new leaves.

The third type of photodynamic herbicidal response elicited by the ALA+2,2'-DP treatment is referred to as a type III response. Based on available data, monocots exhibited this type of response. Although the ALA 2,2'-DP treatment induced the accumulation of significant amounts of tetrapyrrole by the plants, the photodynamic damage was either imperceptible as in wheat, oat, and corn, or when noticeable as in barley, was confined to the upper half of a small proportion of the sprayed plants. In that case the photodynamic damage consisted of small necrotic regions. The seedlings continued to grow vigorously and developed into healthy plants (FIG. 9 H).

FIG. 9 shows Type II and Type III photodynamic herbicidal response of soybean and barley respectively: A,B: control (A) and treated (B) soybean plants after 3 hours of exposure to daylight; C,D: the same control (C) and treated (D) plants after 11 days in the greenhouse; E,F: control (E) and treated (F) barley seedlings after 2 days of exposure to daylight in the greenhouse; G,H: the same control (G) and treated (H) barley plants after 15 days in the greenhouse.

The photodynamic herbicidal formulations described in these examples exhibited an excellent measure of species, age and organ-dependent selectivity. While dicotyledenous weeds such as lambsquarter, mustard, red root pigweed and common purselane were highly susceptible to the tetrapyrrole-induced photodynamic damage, monocots such as corn, wheat, oats, and barley were not adversely affected by the spray. Other dicots were either unaffected by the spray at an early stage of development as in soybean, or recovered fully from a rapid destruction of the primary leaves by producing new and healthy leaves, as was observed for kidney bean, soybean and cotton. Furthermore some tissues which accumulated tetrapyrroles such as bean stems did not exhibit any photodynamic damage. The biochemical basis of this organ, age and species-dependent photodynamic herbicidal selectivity appears to be dependent among other things on the rates of tetrapyrrole turnover and on a differential enhancement of the MV and DV tetrapyrrole biosynthetic pathways in any given plant species.

Example X

MV-Specific Herbicide

MV plant species normally dispose of damaging DV tetrapyrroles by converting them to MV tetrapyrroles, which the plant can metabolize efficiently. However, when sprayed with compounds which inhibit the conversion of DV tetrapyrroles to MV tetrapyrroles, such as 2,4'-DP, or 4,4'-DP, the conversion of DV tetrapyrroles to MV tetrapyrroles is inhibited and the MV plant species accumulates damaging DV tetrapyrroles. Since the MV plants cannot metabolize DV tetrapyrroles efficiently, the DV tetrapyrroles accumulate and create photodynamic damage upon exposure of the plant to light. This is an example of manipulation of the biosynthetic pathway according to the present invention to selectively kill an undesired plant species (in this example, a MV plant).

Giant foxtail (Setaria faberii, a representative monocot) seedlings were germinated and grown as in Example I. Six-day old green seedlings were thinned to 10 plants per container.

Ten-day old seedlings were sprayed in the late afternoon with 0.25 ml of one of the herbicidal compositions A-D below to provide the dosage indicated. Controls were sprayed with solvent only. The solvent used was 0.45 acetone:0.45 ethanol:0.1 Tween 80:9 water (v/v/v/v), adjusted to pH 3.5 with HCl. The plants were wrapped in foil overnight, then the next day were unwrapped and placed in the greenhouse for 10 days, at which time the % photodynamic damage was determined according to the method of Example I.

Figure 10:
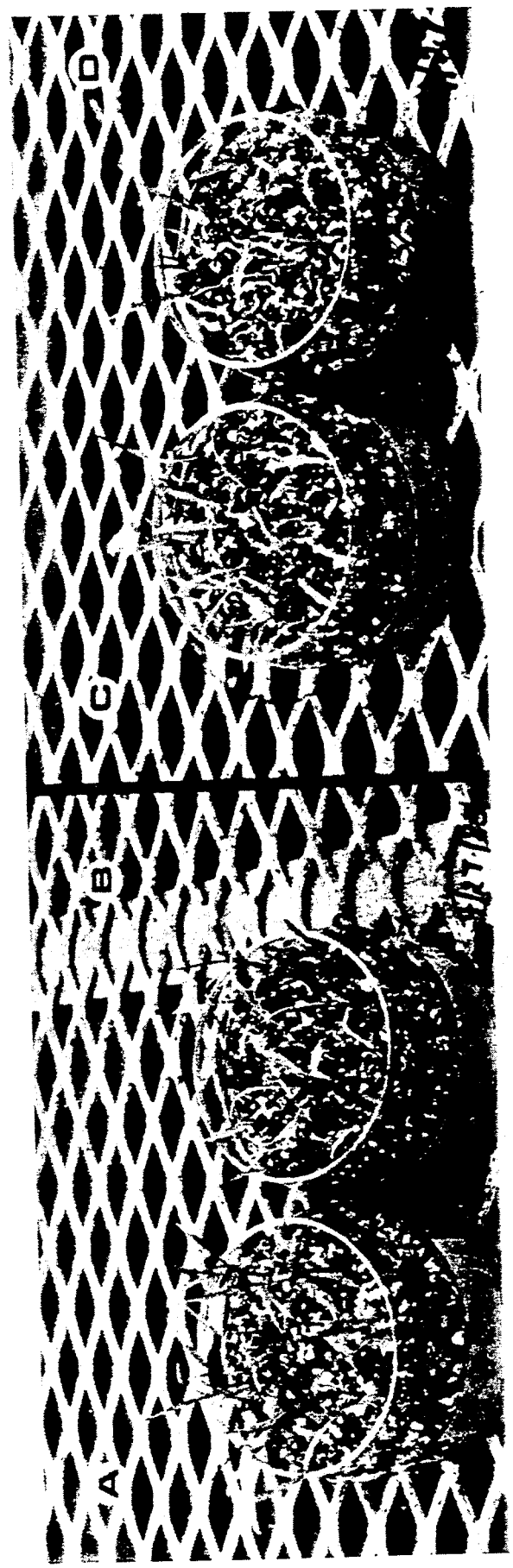
FIG. 10 shows photographs depicting damage to a control plant, a plant treated with ALA, a plant treated with an enhancer, and a plant treated with ALA and an enhancer.

Results are shown in Table IX and in FIG. 10:

TABLE IX

MV Herbicide

| Composition | Treatment (g/acre) | % Photodynamic Damage |
|---|---|---|
| A | 0 (Control) | 0 |
| B | 131 ALA | ≈40 |
| C | 789 2,3'-DP | ≈15 |
| D | 789 2,3'-DP + 131 ALA | ≈70 |

FIG. 10 shows the damage done to the various treated plants after 2 days.

The above results demonstrate the development of a MV-specific herbicides by following experimental protocols as described above.

SECTION II

Solvent Systems

When treated plants are not wrapped in foil (i.e., under greenhouse or field conditions), the solvent may evaporate too rapidly to allow the active component(s) of the herbicidal compositions to penetrate and to translocate to the chloroplasts inside the tissue where tetrapyrrole formation takes place. The following examples describe the development of model greenhouse and field solvent systems.

Example XI

Effects of pH and Timing of Treatment

Cucumber seedlings were germinated and grown as in Example I. Six-day old green seedlings were thinned to 10 plants per container and each container was sprayed with 0.25 ml of one of the herbicidal compositions A-P below to provide the spray rate indicated. The solvent used was 0.45 acetone:0.45 ethanol:0.1 Tween 80:9 water (v/v/v/v) at the indicated pH. The plants were treated in the morning (am) or afternoon (pm) as indicated and left, unwrapped, in the greenhouse for 10 days, at which time the % photodynamic damage was determined according to the method of Example I.

The results are given in Table X:

TABLE X

Effect of pH and Timing of Treatment

| Composition | Treatment (g/acre) | pH | Timing of Treatment | % Photodynamic Damage |
|---|---|---|---|---|
| A | 160 ALA | 6.0 | pm | 0 |
| B | 160 ALA + 240 2,2'-DP | 6.0 | pm | 1 |
| C | 320 ALA | 6.0 | pm | 6 |
| D | 320 ALA + 240 2,2'-DP | 6.0 | pm | 5 |
| E | 160 ALA | 6.0 | am | 1 |
| F | 160 ALA + 240 2,2'-DP | 6.0 | am | 5 |
| G | 320 ALA | 6.0 | am | 1 |
| H | 320 ALA + 240 2,2'-DP | 6.0 | am | 12 |
| I | 160 ALA | 3.5 | pm | 10 |
| J | 160 ALA + 240 2,2'-DP | 3.5 | pm | 30 |
| K | 320 ALA | 3.5 | pm | 60 |
| L | 320 ALA + 240 2,2'-DP | 3.5 | pm | 75 |
| M | 160 ALA | 3.5 | am | 15 |
| N | 160 ALA + 240 2,2'-DP | 3.5 | am | 75 |
| O | 320 ALA | 3.5 | am | 48 |
| P | 320 ALA + 240 2,2'-DP | 3.5 | am | 80 |

The above data indicate a) that when plants are not wrapped in foil, a solvent pH of 3.5 is better than a solvent pH of 6 (i.e., ALA penetrates better in protonated form); and b) it appears that at higher concentrations of ALA enough tetrapyrroles are accumulated even in the presence of sunlight to provide strong herbicidal activity.

Example XII

Methanol Solvent System

Methanol is a cofactor in PChlide synthesis (Rebeiz, C. A., and P. A. Castelfranco, Plant Physiol. 47:24–32 (1971). In order to insure that availability of methanol is not a rate-limiting factor in the synthesis and accumulation of photodynamic tetrapyrroles, exogenous methanol was added to the system in the solvent.

Cucumber seedlings were germinated and grown as in Example I. Six-day old green seedlings were thinned to 10 plants per container and each container was sprayed with 0.25 ml of one of the herbicidal compositions A-L below at the spray rate indicated. The controls were sprayed with solvent only. The solvent used was 0.45 acetone:0.45 methanol:0.1 Tween 80:9 water (v/v/v/v), pH adjusted to 3.5 with HCl. The plants were treated in the morning (am) or afternoon (pm) as indicated and left, unwrapped, in the greenhouse for 10 days, at which time the % photodynamic damage was determined according to the method of Example I.

Results are shown in Table XI:

TABLE XI

Effect of Methyl Alcohol in Solvent

| Composition | Treatment (g/acre) | Timing of Treatment | % Photodynamic Damage |
|---|---|---|---|
| A | Control | pm | 0 |
| B | 160 ALA | pm | 15 |
| C | 160 ALA + 240 2,2'-DP | pm | 80 |
| D | Control | pm | 0 |
| E | 320 ALA | pm | 85 |
| F | 320 ALA + 240 2,2'-DP | pm | 93 |
| G | Control | am | 0 |
| H | 160 ALA | am | 13 |
| I | 160 ALA + 240 2,2'-DP | am | 85 |
| J | Control | am | 0 |
| K | 320 ALA | am | 65 |
| L | 320 ALA + 240 2,2'-DP | am | 98 |

Comparison with the pH 3.5 treatment in Table X shows that substitution of methanol for ethanol in the solvent system consisting of 0.45 acetone:0.45 ethanol:0.1 Tween 80:9 water (v/v/v/v) resulted in increased photodynamic damage.

Example XIII

Tween 80 Solvent System

Tween 80 is a well-known surfactant available from a variety of sources (e.g., Nutritional Biochemical Corp., Cleveland, Ohio). It usually facilitates the translocation of sprayed herbicides from the surface of the tissue to the site of action.

Cucumber seedlings were germinated and grown as in Example I. Six-day old green seedlings were thinned to 10 plants per container and each container was sprayed at the time indicated with 0.25 ml of herbicide to provide 130 g ALA+390 g 2,2'-DP/acre in the solvents indicated below. All solvents were adjusted to pH 3.5 with dilute HCl. All plants except C and H were placed unwrapped in the greenhouse for 10 days, at which time the % photodynamic damage was determined according to Example I. In experiments C and H, the treated plants were initially wrapped in foil and incubated in the dark overnight at 28° C. as in Example I before being unwrapped and left in the greenhouse with the others.

Results are shown in Table XII:

TABLE XII

Effect of Tween 80 in Solvent

| Experiment | Solvent | Timing of Treatment | Wrapped | % Photo-dynamic Damage |
|---|---|---|---|---|
| A | Water | pm | No | 62 |
| B | 0.1 Tween 80: 99.9 water (v/v) | pm | No | 35 |
| C | 0.1 Tween 80: 99.9 water (v/v) | pm | Yes | 100 |
| D | 0.5 Tween 80: 99.5 Water (v/v) | pm | No | 88 |
| E | 1 Tween 80: 99 water (v/v) | pm | No | 70 |
| F | Water | am | No | 66 |
| G | 0.1 Tween 80: 99.9 water (v/v) | am | No | 76 |
| H | 0.1 Tween 80: 99 water (v/v) | pm | Yes | 100 |
| I | 0.5 Tween 80: 99.5 water (v/v) | am | No | 85 |
| J | 1 Tween 80: 9 water (v/v) | am | No | 76 |

Tween 80 exhibited the best effect at 0.5–1% (v/v) both in the morning and afternoon sprays.

Example XIV

Polyethylene Glycol Solvent System

Polyethylene glycol (PEG) leaves a thin protective film when sprayed on tissue surfaces; accordingly, it was added to the solvent to determine whether such a film will slow down solvent evaporation and permit a better translocation of the ALA+2,2'-DP to the chloroplasts.

Cucumber seedlings were germinated and grown as in Example I. Six-day old green seedlings were thinned to 10 plants per container and each container was sprayed at the time indicated with 0.25 ml of one of compositions A–L below at the spray rate indicated. The controls were sprayed with 0.25 ml of solvent only. The solvent was 0.9 PEG 600:0.1 Tween 80:9 water (v/v/v), pH 3.5. The plants were placed unwrapped in the greenhouse for 10 days, at which time the % photodynamic damage was determined according to Example I. In Experiments C and I, the treated plants were initially wrapped in foil and incubated in the dark overnight at 28° C. as in Example I; the next morning they were unwrapped and left in the greenhouse with the others.

Results are shown in Table XIII:

TABLE XIII

Effect of PEG on Solvent System

| Composition | Treatment (g/acre) | Timing of Treatment | Wrapped | % Photo-dynamic Damage |
|---|---|---|---|---|
| A | Control | pm | No | 0 |
| B | 80 ALA + 240 2,2'-DP | pm | No | 88 |
| C | 80 ALA + 240 2,2'-DP | pm | Yes | 100 |
| D | Control | pm | No | 0 |
| E | 160 ALA | pm | No | 83 |
| F | 160 ALA + 240 2,2'-DP | pm | No | 95 |
| G | Control | am | No | 0 |
| H | 80 ALA + 240 2,2'-DP | am | No | 85 |
| I | 80 ALA + 240 2,2'-DP | pm | Yes | 100 |
| J | Control | am | No | 0 |
| K | 160 ALA | am | No | 63 |
| L | 160 ALA + 240 2,2'-DP | am | No | 78 |

PEG appeared to be beneficial when incorporated into formulations containing water and Tween 80 (compare Table XII (E) and (J) to Table XIII (B) and (H), respectively).

Example XV

PEG and Methanol Solvent System

Cucumber seedlings were germinated and grown as in Example I. Six-day old green seedlings were thinned to 10 plants per container and each container was sprayed with 0.25 ml of herbicidal composition to provide a spray rate of 80 g ALA+240 g 2,2'-DP/acre in the solvents indicated below. All solvents were adjusted to pH 3.5 with dilute HCl. The plants were treated in the morning or afternoon as indicated and left, unwrapped, in the greenhouse for 10 days, at which time the % photodynamic damage was determined according to the method of Example I.

Results are shown in Table XIV:

TABLE XIV

Effect of PEG and Methanol in Solvent

| Experiment | Solvent | Timing of Treatment | % Photo-dynamic Damage |
|---|---|---|---|
| A | 0.9 PEG:0.1 Tween 80: 9 water (v/v/v) | pm | 70 |

TABLE XIV-continued
Effect of PEG and Methanol in Solvent

| Experiment | Solvent | Timing of Treatment | % Photo-dynamic Damage |
|---|---|---|---|
| B | 0.7 PEG:0.2 methanol: 0.1 Tween 80:9 water (v/v/v/v) | pm | 65 |
| C | 0.5 PEG:0.4 methanol: 0.1 Tween 80:9 water (v/v/v/v) | pm | 35 |
| D | 0.3 PEG:0.6 methanol: 0.1 Tween 80:9 water (v/v/v/v) | pm | 40 |
| E | 0.1 PEG:0.8 methanol: 0.1 Tween 80:9 water (v/v/v/v) | pm | 38 |
| F | 0.9 methanol:0.1 Tween 80:9 water (v/v/v) | pm | 13 |
| G | 0.9 PEG:0.1 Tween 80: 9 water (v/v/v) | am | 78 |
| H | 0.7 PEG:0.2 methanol: 0.1 Tween 80:9 water (v/v/v/v) | am | 63 |
| I | 0.5 PEG:0.4 methanol: 0.1 Tween 80:9 water (v/v/v/v) | am | 53 |
| J | 0.3 PEG:0.6 methanol: 0.1 Tween 80:9 water (v/v/v/v) | am | 65 |
| K | 0.1 PEG:0.8 methanol: 0.1 Tween 80:9 water (v/v/v/v) | am | 68 |
| L | 0.9 methanol:0.1 Tween 80:9 water (v/v/v) | am | 50 |

None of the just-described formulations provided to be superior to those containing only PEG at the low ALA concentrations used in these experiments. However, morning sprays proved superior to afternoon sprays (compare A-F to G-L).

Example XVI

PEG and Methanol Solvent System at Higher ALA Concentrations

Cucumber seedlings were germinated and grown as in Example I. Six-day old green seedlings were thinned to 10 plants per container and each container was sprayed at the time indicated with 0.25 ml of one of the herbicidal compositions A-HH below to provide the spray rate indicated. Controls were treated with 0.25 ml solvent only. The solvent used was 0.7 PEG:0.2 methanol:0.1 Tween 80:9 water (v/v/v/v) pH 3.5. The plants were placed unwrapped in the greenhouse for 10 days, at which time the % photodynamic damage was determined according to Example I. In experiments O, R, AA, and DD, the treated plants were initially wrapped in foil and incubated in the dark overnight at 28° C. as in Example I before being unwrapped the next day and placed with the others.

The results are shown in Table XV:

TABLE XV
Effect of PEG and Methanol at Higher Concentrations of ALA

| Composition | Treatment (g/acre) | Time of Treatment | Wrapped | % Photo-dynamic Damage |
|---|---|---|---|---|
| A | Control | pm | No | 0 |
| B | 160 ALA | pm | No | 20 |
| C | 160 ALA + 240 2,2'-DP | pm | No | 80 |
| D | Control | pm | No | 0 |
| E | 320 ALA | pm | No | 83 |
| F | 320 ALA + 240 2,2'-DP | pm | No | 90 |
| G | Control | am | No | 0 |
| H | 160 ALA | am | No | 43 |
| I | 160 ALA + 240 2,2'-DP | am | No | 95 |
| J | Control | am | No | 0 |
| K | 320 ALA | am | No | 95 |
| L | 320 ALA + 240 2,2'-DP | am | No | 100 |
| M | Control | pm | No | 0 |
| N | 130 ALA + 130 2,2'-DP | pm | No | 20 |
| O | 130 ALA + 130 2,2'-DP | pm | Yes | 100 |
| P | Control | pm | No | 0 |
| Q | 130 ALA + 260 2,2'-DP | pm | No | 85 |
| R | 130 ALA + 260 2,2'-DP | pm | Yes | 100 |
| S | Control | am | No | 0 |
| T | 130 ALA | am | No | 5 |
| U | 130 2,2'-DP | am | No | 3 |
| V | 130 ALA + 130 2,2'-DP | am | No | 38 |
| W | 130 ALA + 260 2,2'-DP | am | No | 85 |
| X | 130 ALA + 390 2,2'-DP | am | No | 87 |
| Y | 130 2,2'-DP | pm | No | 5 |
| Z | 260 ALA + 130 2,2'-DP | pm | No | 58 |
| AA | 260 ALA + 130 2,2'-DP | pm | Yes | 80 |
| BB | 260 2,2'-DP | pm | No | 5 |
| CC | 260 ALA + 260 2,2'-DP | pm | No | 55 |
| DD | 260 ALA + 260 2,2'-DP | pm | Yes | 80 |
| EE | 130 2,2'-DP | am | No | 30 |
| FF | 260 ALA + 130 2,2'-DP | am | No | 78 |
| GG | 260 2,2'-DP | am | No | 30 |
| HH | 260 ALA + 260 2,2'-DP | am | No | 95 |

(a) At the higher ALA concentrations, the PEG plus methanol formulation was more effective in the morning spray than in the afternoon spray; (b) the morning spray was better than formulations containing either methanol alone (Table XI) or PEG alone (Table XIII).

Example XVII

Ethylene Glycol Solvent Systems

Cucumber seedlings were germinated and grown as in Example I. Six-day old green seedlings were thinned to 10 plants per container and each container was sprayed with 0.25 ml of one of the herbicidal compositions A-D below at the spray rate indicated. The solvent used was 0.45 acetone:0.45 ethanol:0.2 Tween 80:0.9 ethylene glycol:18 water (v/v/v/v/v), pH 3.5. The plants were treated in the afternoon and left, unwrapped, in the greenhouse for 10 days, at which time the % photodynamic damage was determined according to the method of Example I.

Results are shown in Table XVI:

TABLE XVI
Ethylene Glycol-Based Solvent System

| Composition | Treatment (g/acre) | % Photo-dynamic Damage |
|---|---|---|
| A | 160 ALA | 30 |
| B | 160 ALA + 240 2,2'-DP | 85 |
| C | 320 ALA | 100 |
| D | 320 ALA + 480 2,2'-DP | 100 |

These preliminary results indicate that ethylene glycol is also a desirable adjuvant for the ALA+2,2'-DP herbicidal formulation.

SECTION III

Field Spray System

Translation of the greenhouse formulations to specific field situations is straightforward.

Example XVIII

Control of Broadleaf Weeds in Lawn

Figure 11A:
FIG. 11 (FIGS. 11A to 11F) shows photographs depicting control of broadleaf weeds by the invention.
Figure 11B:

Field lots (0.25 m$^2$) of Kentucky blue grass plus red fescue infested with "creeping Charley" (*Glecoma hederacea*) and plantain (*Plantago lanceolata*) were staked out. A representative lot (Lot 1) was photographed on May 22, 1985 (FIG. 11(A)) and Jun. 4, 1985 (FIG. 11(B)) to show the progress of broadleaf weed infestation over a 16-day period.

Figure 11C:
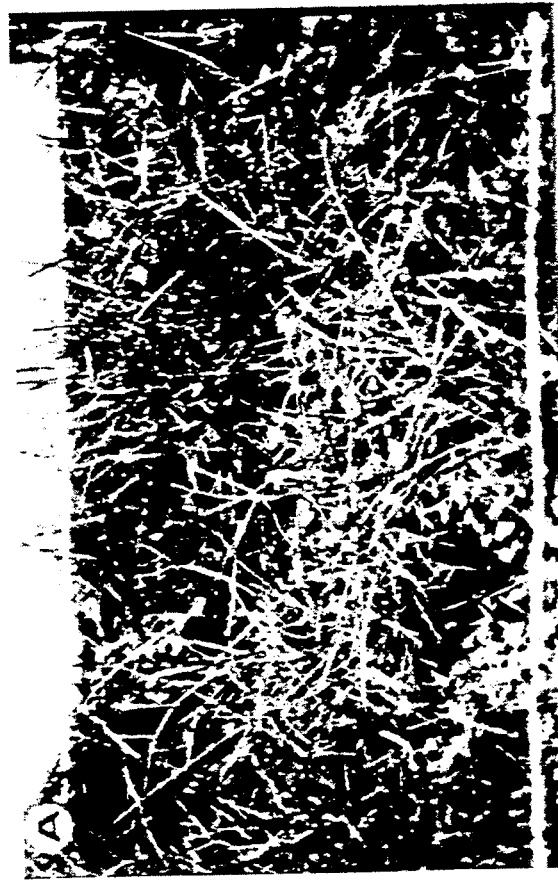
Figure 11D:

A second lot was sprayed in the late afternoon on May 22, 1985 with 10 ml to yield a dosage rate of 525 g ALA +390 g 2,2'-DP/acre in 0.1 Tween 80:9.9 water (v/v), adjusted to pH 4.5 with dilute HCl. The treatment was repeated on May 30, 1985. FIG. 11(C) shows the sprayed lot on May 22, 1985, demonstrating the extend of infestation at spray time FIG. 11(D) shows the same sprayed lot on Jun. 4, 1985, showing 95% photodynamic damage (calculated according to the method of Example I) of all broadleaf weeds in the treated area. Note the survival of the bluegrass, unscathed.

Figure 11F:
Figure 11E:

Lot 3 was sprayed once on the afternoon of May 20, 1985, with 10 ml to yield a dosage rate of 525 g ALA+390 g 2,2'-DP/acre in 0.7 PEG 600:0.2 methanol:0.1 Tween 80:9 water (v/v/v/v), adjusted to pH 3.5 with HCl. No results were obtained because this solvent system is not appropriate for afternoon spraying. By contrast, when Lot 4 was sprayed once in the morning of Jul 01, 1985 with the same formulation as Lot 3 above, results were FIG. 11(E) shows the treated lot on Jun. 1, 1985 just after spraying. FIG. 11(F) shows the same treated lot on Jun. 9, 1985, showing 95% photodynamic damage (calculated according to the procedure of Example I) of all broadleaf weeds in the treated area. Again, note the survival of the bluegrass.

SECTION IV

Soil Application

Example XIX

Uptake of ALA+2,2'-DP by Roots of Plants

Cucumber seedlings were germinated and grown as in Example I. Six-day old green seedlings were thinned to 10 plants per container.

20 mM ALA+15 mM 2,2'-DP solution was prepared in 0.45 acetone:0.45 ethanol:0.1 Tween 80:9 water (v/v/v/v) and the pH was adjusted to 3.5 with HCl. The indicated amounts of this composition were added to the vermiculite of 8-day old plants int he greenhouse in the late afternoon. Control plants were treated with solvent only. The plants were placed unwrapped in the greenhouse for 10 days, at which time the % photodynamic damage was determined according to the method of Example I.

Figure 12:
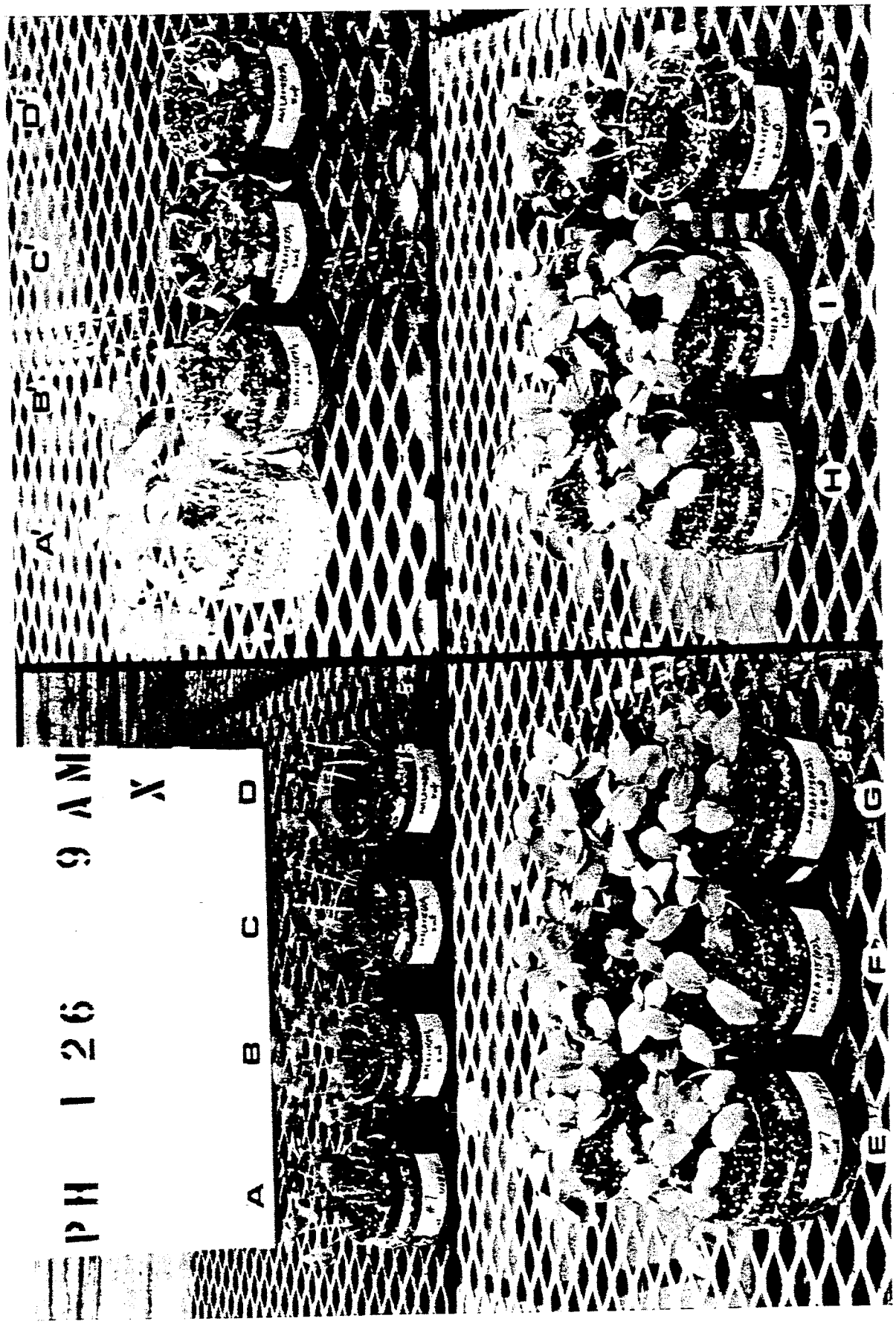
FIG. 12 shows photographs depicting control plants, plants treated with ALA plus an enhancer via soil, and damage done by root uptake.

Results are shown in Table XVII and in FIG. 12:

TABLE XVII

| Composition | Ml of 20 mM ALA + 15 mM 2,2'-DP | Application Rate (per acre) | % Photo-dynamic Damage |
|---|---|---|---|
| A | 0(Control:5 ml solvent only) | 0(Control) | 0 |
| B | 2 | 4.2 kg ALA + 3.2 kg 2,2'-DP | 100 |
| C | 3 | 6.3 kg ALA + 4.8 kg 2,2'-DP | 100 |
| D | 5 | 10.5 kg ALA + 8 kg 2,2'-DP | 100 |
| E | 0(Control:2 ml solvent only) | 0(Control) | 0 |
| F | 0.25 | 526 g ALA + 394 g 2,2'-DP | 0 |
| G | 0.5 | 1.05 kg ALA + 788 g 2,2'-DP | 0 |
| H | 0(Control:2 ml solvent only) | 0(Control) | 0 |
| I | 1 | 2.1 kg ALA + 1.6 kg 2,2'-DP | 0 |
| J | 2 | 4.2 kg ALA + 3.2 kg 2,2'-DP | 60 |

FIG. 12 shows the damage done by compositions A, B, C, and D the following morning (A, B, C, D) and two days later (A', B') and by all compositions 2 days later (F–J).

It appears that ALA+2,2'-DP when applied to the medium in which the plants are growing can be taken up by the roots and translocated upward. The photodynamic damage appears to be most prominent in the hypocotyls as shown in FIG. 12.

SECTION V

Pre-Emergence Spray

Example XX

Effect on Seed Germination

Ten cucumber seeds were planted in vermiculite in each of several glass containers (9 cm deep×9 cm in diameter). The seeds were watered and various amounts of 10 mM ALA+7.5 mM 2,2'-DP in 0.45 acetone:0.45 ethanol:0.1 Tween 80:9 water (v/v/v/v), pH 3.0 were added as indicated. Controls were treated with solvent only. The containers were left unwrapped in the greenhouse for 2 weeks, at which time the % germination was determined.

Results are given in Table XVIII:

TABLE XVIII

| Composition | Ml 10 mM ALA + 7.5 mM 2,2'-DP | Application Rate (per acre) | % Germination |
|---|---|---|---|
| A | 0.5 ml solvent | 0(Control) | 90 |
| B | 0.5 ml | 524 g ALA + 393 g 2,2'-DP | 100 |
| C | 1 ml solvent | 0(control) | 100 |
| D | 1 ml | 1.05 kg ALA + 788 g 2,2'-DP | 90 |
| E | 4 ml solvent | 0(Control) | 80 |
| F | 4 ml | 4.2 kg ALA + 3.15 kg 2,2'-DP | 0 |

It appears from the above data that ALA+2,2'-DP at very high concentrations can act as a pre-emergence herbicide.

SECTION VI

Interaction of the ALA System With Other Herbicides

Interaction with other herbicides was found to be either additive, synergistic, or antagonistic, as described below.

Example XXI

Interaction with Other Herbicides

Cucumber seedlings were germinated and grown as in Example I. Six-day old green seedlings were thinned to 10 plants per container and sprayed in the late afternoon with 0.25 ml of one of the herbicidal compositions A-L below at the spray rate indicated. Controls were sprayed with solvent only. The solvent was 0.45 acetone:0.45 ethanol:0.1 Tween 80:9 water (v/v/v/v), adjusted to pH 3.5 with HCl. The plants were wrapped in foil overnight, then the next day unwrapped and placed in the greenhouse for 10 days, at which time the photodynamic damage was determined according to the method of Example I.

Figures 1, 13:
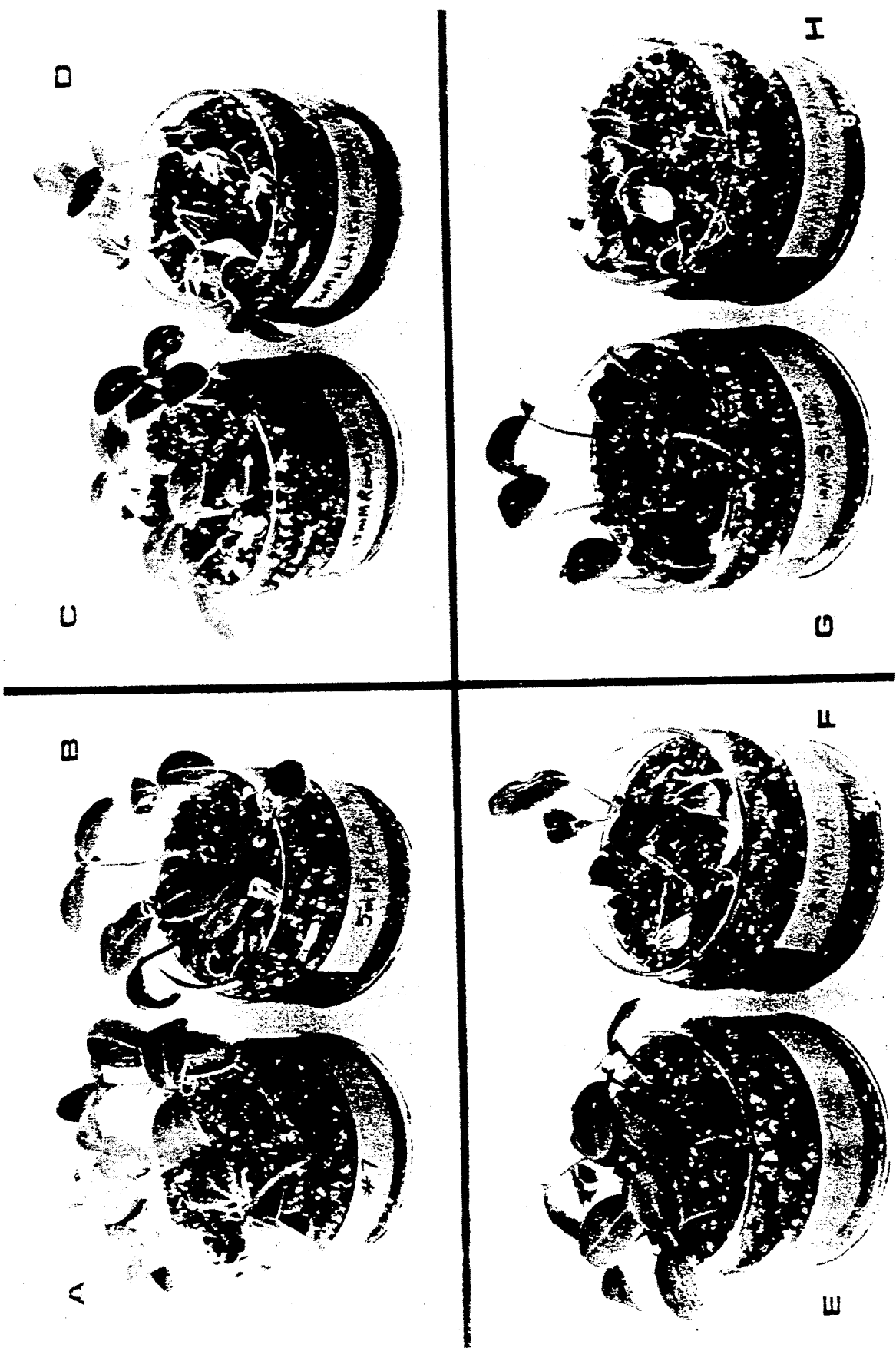
FIG. 13 (FIGS. 13-1 and 13-2) shows photographs depicting control plants, plants treated with ALA, and plants treated with ALA plus an herbicide.
Figures 2, 13:
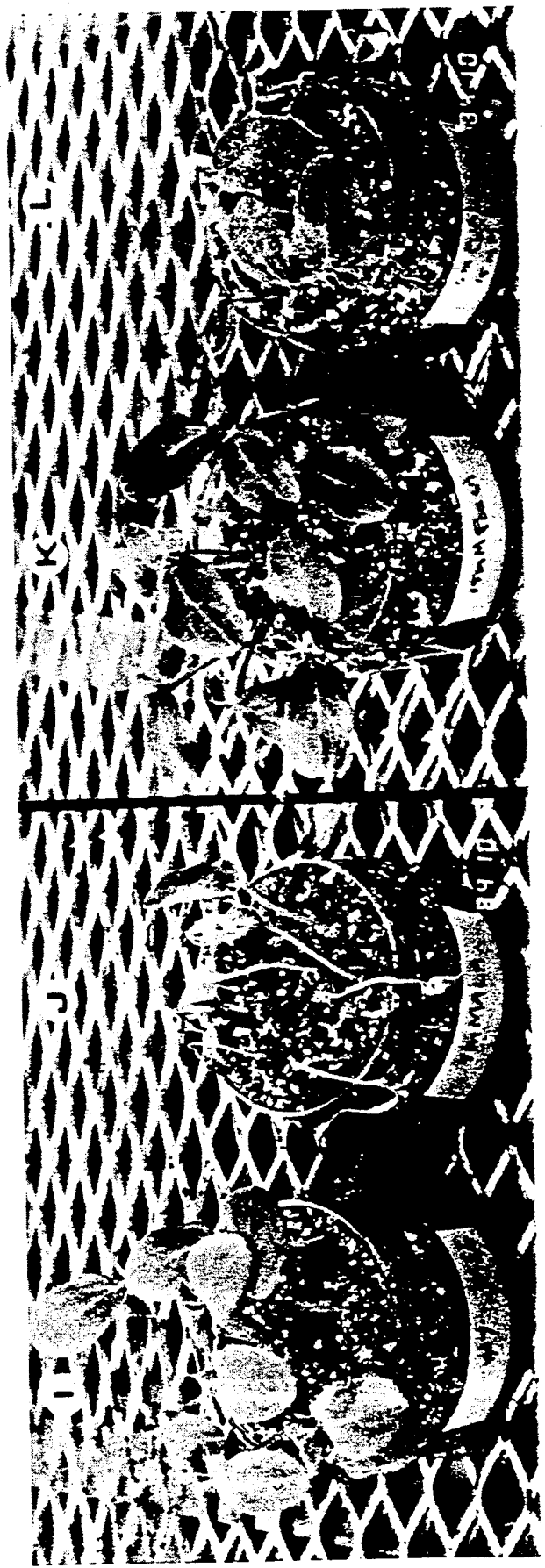

Results are shown in Table XIX and in FIG. 13:

TABLE XIX

| | Other Herbicides | |
|---|---|---|
| Composition | Treatment (g/acre) | % Photodynamic Damage |
| A | Control | 0 |
| B | 114 ALA | 46 |
| C | 398 Roundup ™ [1] | 50 |
| D | 114 ALA + 398 Roundup | 100 |
| E | Control | 0 |
| F | 114 ALA | 57 |
| G | 490 Sutan Plus ™ [2] | 15 |
| H | 114 ALA + 490 Sutan Plus | 90 |
| I | Control | 0 |
| J | 114 ALA | 70 |
| K | 771 Poast ™ [3] | 0 |
| L | 114 ALA + 771 Poast | 20 |

[1]Glyphosate MON-0573, Monsanto Co., St. Louis, MO
[2]R-25788, Stauffer Chemicals, Westport, CT
[3]sethoxydin, BAS 90520H, BASF/Nippon Soda, W. Germany FIG. 13 shows damage done to treated plants after 5 days.

SECTION VII

Interaction of the ALA System With Porphyria-Inducing Drugs

Porphyria is a metabolic dysfunction which results in the accumulation of photodynamic tetrapyrroles in the various tissues of the human body. Certain drugs routinely used in various medical treatments are suspected of triggering porphyric attacks in susceptible patients. In order to determine whether such drugs could act as enhancers and/or inducers of ALA, their potential herbicidal effectiveness in conjunction with ALA was investigated.

Example XXII

Porphyria-Inducing Drugs

Cucumber seedlings were germinated and grown as in Example I. Six-day old green seedlings were thinned to 10 plants per container and sprayed in the late afternoon with 0.25 ml of one of the herbicidal compositions A-X below at the spray rate indicated. Controls were sprayed with solvent only. The solvent was 0.45 acetone:0.45 ethanol:0.1 Tween 80:9 water (v/v/v/v), adjusted to pH 3.5 with HCl. The plants were wrapped in foil overnight, then the next day unwrapped and placed in the greenhouse for 10 days, at which time the photodynamic damage was determined according to the method of Example I.

Results are shown in Table XX:

TABLE XX

| | Porphyria-Inducing Drugs | |
|---|---|---|
| Experiment | Treatment (g/acre) | % Photodynamic Damage |
| A | Control | 0 |
| B | 131 ALA | 83 |
| C | 377 meprobamate[1] | 0 |
| D | 131 ALA + 377 meprobamate | 88 |
| E | 377 L-alpha-methyldopa[2] | 0 |
| F | 131 ALA + 377 L-alpha-methyldopa | 55 |
| G | 377 phenobarbital[3] | 0 |
| H | 131 ALA + 377 phenobarbital | 95 |
| I | Control | 0 |
| J | 131 ALA | 42 |
| K | 377 glutethimide[4] | 0 |
| L | 131 ALA + 377 glutethimide | 45 |
| M | 377 conjugated estrogen[5] | 0 |
| N | 131 ALA + 377 conjugated estrogen | 17 |
| O | 377 ergotamine tartrate[6] | 0 |
| P | 131 ALA + 377 ergotamine tartrate | 23 |
| Q | Control | 0 |
| R | 131 ALA | 43 |
| S | 377 extended phenytoin sodium[7] | 0 |
| T | 131 ALA + 377 extended phenytoin sodium | 50 |
| U | 377 (sulfisoxazold)Roche[8] | 0 |
| V | 131 ALA + 377 (sulfisoxazold)Roche | 43 |
| W | 377 tolbutamide[9] | 0 |
| X | 131 ALA + 377 tolbutamide | 40 |

[1]Equanil ™, Wyeth Labs, Philadelphia, PA
[2]Aldomet ™, Merck Sharp & Dohme, West Point, PA
[3]available from a variety of sources, e.g. Sigma Chemical Co., St. Louis, MO
[4]Doriden ™, USV Development Corp., Manati, PR
[5]Permarin ™, Ayerst Labs, New York, NY
[6]Ergomar ™, Parke-Davis, Morris Plains, NJ
[7]Dilantin ™, Parke-Davis
[8]Granticin ™, Hoffman-LaRoche, Nutley, NJ
[9]Orinase ™, UpJohn Co., Kalamazoo, MI In general, none of the drugs that were tested proved to be significant inducers or enhancers of ALA.

These examples serve to demonstrate the novel herbicidal concept of the present invention. The photodynamic mode of action is different from other known herbicidal modes of action in two main respects: (a) it is dependent on the biosynthesis and accumulation of tetrapyrroles by living green plants; and (b) the accumulated tetrapyrroles render the plants light-sensitive so that upon subsequent exposure to light a very damaging photodynamic effect is produced, which on a clear day results in the death of susceptible plants in a matter of hours.

δ-Aminolevulinic acid is a natural metabolite present in all living cells; it is a natural component of the biosphere and is readily biodegradable. The same is true for the products of ALA dark-metabolism, i.e., for the tetrapyrrole intermediates of the Chl biosynthetic pathway, which have been demonstrated to disappear very rapidly upon exposure of the plant to light. It therefore appears that the photodynamic herbicidal compositions and methods of the present invention are likely to have no adverse impact on the environment.

Further examples of compositions and applications within the spirit and scope of this invention will be apparent to those skilled in this art upon consideration of the foregoing and consequently only such limitations as appear in the appended claims should be placed thereon.

We claim:

1. A composition comprising δ-aminolevulinic acid, and at least one compound selected from the group consisting f inducers of δ-aminolevulinic acid, enhancers of δ- aminolevulinic acid conversion to photodynamic tetrapyrroles, and inhibitors of conversion of divinyl tetrapyrroles to monovinyl tetrapyrroles at a concentration of from about 2 to bout 30 mM of δ-aminolevulinic acid and about 10 to about 30 mM of the compound selected from the group consisting of inducers of δ-aminolevulinic acid, enhancers of δ-aminolevulinic acid conversion to photodynamic tetrapyrroles, and inhibitors of conversion of divinyl tetrapyrroles to monovinyl tetrapyrroles.

2. The composition of claim 1 comprising δ-aminolevulinic acid and at least one inducer of δ-aminolevulinic acid.

3. The composition of claim 1 comprising δ-aminolevulinic acid and at least one enhancer of δ-aminolevulinic acid conversion to photodynamic tetrapyrroles.

4. The composition of claim 1 comprising δ-aminolevulinic acid and at least one inhibitor of conversion of divinyl tetrapyrroles to monovinyl tetrapyrroles.

5. The composition of claim 1 comprising δ-aminolevulinic acid and at least one inducer of δ-aminolevulinic acid and at least one enhancer of conversion of δ-aminolevulinic acid to photodynamic tetrapyrroles.

6. The composition of claim 1 comprising δ-aminolevulinic acid and at least one inducer of δ-aminolevulinic acid and at least one inhibitor of conversion of divinyl tetrapyrroles to monovinyl tetrapyrroles.

7. The composition of claim 1 comprising δ-aminolevulinic acid and at least one enhancer of δ-aminolevulinic acid conversion to photodynamic tetrapyrroles and at least one inhibitor of conversion of divinyl tetrapyrroles to monovinyl tetrapyrroles.

8. The composition of claim 1 further comprising at least one of the following: carrier(s), solvent(s), buffer(s), wetting agent(s), dispersing agent(s), defoaming agent(s), emetic(s), stench(es), penetrant(s), surfactant(s), emulsifier(s), and adjuvant(s).

9. The composition of claim 1 comprising δ-aminolevulinic acid and at least one inducer of δ-aminolevulinic acid and at least one enhancer of δ-aminolevulinic acid conversion to photodynamic tetrapyrroles and at least one inhibitor of conversion of divinyl tetrapyrroles to monovinyl tetrapyrroles.

10. The composition of claim 1 wherein said δ-aminolevulinic acid is present in a concentration of at least 15 mM.

11. The herbicidal composition of claim 1 wherein said undesirable plant is selected from the group consisting of *Chenopodium album*, *Brassica kaber/juncea*, *Amaranthus retroflexus*, *Portulaca oleracea*, *Glecoma hederacea*, *Setaria faberii*, and *Plantago lanceolata*.

12. A method for inducing the accumulation of photodynamic tetrapyrroles in a whole green plant, said method comprising contacting said plant with an amount effective for accumulating photodynamic tetrapyrroles in a whole, green plant of a composition comprising δ-aminolevulinic acid in combination with at least one compound selected from the group consisting of inducers of δ-aminolevulinic acid, enhancers of conversion of δ-aminolevulinic acid to photodynamic tetrapyrroles, and inhibitors of conversion of divinyl tetrapyrroles to monovinyl tetrapyrroles.

13. The method of claim 12 wherein in the said composition there is a concentration of from about 2 to about 30 mM of δ-aminolevulinic acid and about 10 to about 30 mM of the compound selected from the group consisting of inducers of δ-aminolevulinic acid, enhancers of δ-aminolevulinic acid conversion to photodynamic tetrapyrroles, and inhibitors of conversion of divinyl tetrapyrroles to monovinyl tetrapyrroles.

14. The method of claim 13 wherein said composition comprises δ-aminolevulinic acid and at least one inducer of δ-aminolevulinic acid.

15. The method of claim 13 wherein said composition comprises δ-aminolevulinic acid and at least one enhancer of δ-aminolevulinic acid conversion to photodynamic tetrapyrroles.

16. The method of claim 13 wherein said composition comprises δ-aminolevulinic acid and at least one inhibitor of conversion of divinyl tetrapyrroles to monovinyl tetrapyrroles.

17. The method of claim 13 wherein said composition comprises δ-aminolevulinic acid and at least one inducer of δ-aminolevulinic acid and at least one enhancer of conversion of δ-aminolevulinic acid to photodynamic tetrapyrroles.

18. The method of claim 13 wherein said composition comprises δ-aminolevulinic acid and at least one inducer of δ-aminolevulinic acid and at least one inhibitor of conversion of divinyl tetrapyrroles to monovinyl tetrapyrroles.

19. The method of claim 13 wherein said composition comprises δ-aminolevulinic acid and at least one enhancer of δ-aminolevulinic acid conversion to photodynamic tetrapyrroles and at least one inhibitor of conversion of divinyl tetrapyrroles to monovinyl tetrapyrroles.

20. The method of claim 12 wherein the composition further comprises at least one of the following: carrier(s), solvent(s), buffer(s), wetting agent(s), dispersing agent(s), defoaming agent(s), emetic(s), stench(es), penetrant(s), surfactant(s), emulsifier(s), and adjuvant(s).

21. The method of claim 13 wherein said composition comprises δ-aminolevulinic acid and at least one inducer of δ-aminolevulinic acid and at least one enhancer of δ-aminolevulinic acid conversion to photodynamic tetrapyrroles and at least one inhibitor of conversion of divinyl tetrapyrroles to monovinyl tetrapyrroles.

22. The method of claim 12 wherein said δ-aminolevulinic acid is present in a concentration of at least 15 mM.

23. The method of claim 12 wherein said treated plant is exposed to a substantial absence of light at wavelengths of 300 to 700 nm.

24. The method of claim 23 wherein said treated plant is exposed to said substantial absence of light for about 1 to 8 hours.

25. The method of claim 12 wherein a seed of said plant is contacted with said effective amount.

26. The method of claim 12 wherein said plant is contacted with said effective amount by application of said effective amount to the medium in which said plant is growing.

27. The method of claim 26 wherein said plant is growing in soil.

28. The method of claim 12 wherein said plant is contacted with said effective amount by application of said effective amount to the roots of said plant.

29. A method of controlling undesirable, whole, green plants, said method comprising:
   (a) contacting an undesirable, whole, green plant with a herbicidally effective amount, for controlling an undesirable, whole, green plant of a composition comprising δ-aminolevulinic acid in combination with at least one compound selected from the group consisting of inducers of δ-aminolevulinic acid, enhancers of δ-aminolevulinic acid conversion to photodynamic tetrapyrroles, and inhibitors of conversion of divinyl tetrapyrroles to monovinyl tetrapyrroles, and
   (b) exposing the treated plant of step (a) to light.

30. The method of claim 29 wherein in the said composition in step (a) there is a concentration of from about 2 to about 30 mM of δ-aminolevulinic acid and about 10 to about 30 mM of the compound selected from the group consisting of inducers of δ-aminolevulinic acid, enhancers of δ-aminolevulinic acid conversion to photodynamic tetrapyrroles, and inhibitors of conversion of divinyl tetrapyrroles to monovinyl tetrapyrroles.

31. The method of claim 30 wherein said composition in step (a) comprises δ-aminolevulinic acid and at least one inducer of δ-aminolevulinic acid.

32. The method of claim 30 wherein said composition in step (a) comprises δ-aminolevulinic acid and at least one enhancer of δ-aminolevulinic acid conversion to photodynamic tetrapyrroles.

33. The method of claim 30 wherein said composition in step (a) comprises δ-aminolevulinic acid and at least one inhibitor of conversion of divinyl tetrapyrroles to monovinyl tetrapyrroles.

34. The method claim 30 wherein said composition in step (a) comprises δ-aminolevulinic acid and at least one inducer of δ-aminolevulinic acid and at least one enhancer of conversion of δ-aminolevulinic acid conversion to photodynamic tetrapyrroles.

35. The method of claim 30 wherein said composition in step (a) comprises δ-aminolevulinic acid and at least one inducer of δ-aminolevulinic acid and at least one inhibitor of conversion of divinyl tetrapyrroles to monovinyl tetrapyrroles.

36. The method claim 30 wherein said composition in step (a) comprises δ-aminolevulinic acid and at least one enhancer of δ-aminolevulinic acid conversion to photodynamic tetrapyrroles and at least one inhibitor of conversion of divinyl tetrapyrroles to monovinyl tetrapyrroles.

37. The method claim of 29 wherein the composition of step (a) further comprises at least one of the following: carrier(s), solvent(s), buffer(s), wetting agent(s), dispersing agent(s), defoaming agent(s) emetic(s), stench(es), penetrant(s), surfactant(s), emulsifier(s), and adjuvant(s).

38. The method of claim 29 wherein said treated plant of step (a) is exposed to a substantial absence of light at wavelengths of 300 to 700 nm before being exposed to light in step (b).

39. The method of claim 29 wherein said plant is exposed to light in step (b) for a period of time sufficient to oxidize most unsaturated membrane lipoproteins of said plant.

40. The method of claim 30 wherein said composition in step (a) comprises δ-aminolevulinic acid, at lest one inducer of δ-aminolevulinic acid, at least one enhancer of δ-aminolevulinic acid conversion to photodynamic tetrapyrroles, and at least one inhibitor of conversion of divinyl tetrapyrroles to monovinyl tetrapyrroles.

41. The method of claim 38 wherein said treated plant of step (a) is exposed to said substantial absence of light for about 1 to 8 hours before being exposed to light in step (b).

42. The method of claim 39 wherein said plant is exposed to light in step (b) in the form of natural daylight for a period of about 1 to 14 days.

43. The method of claim 29 wherein said δ-aminolevulinic acid is present in a concentration of at least 15 mM.

44. The method of claim 29 wherein said undesirable plant is selected from the group consisting of *Chenopodium album*, *Brassica kaber/juncea*, *Amaranthus retroflexus*, *Portulaca oleracea*, *Glecoma hederacea*, *Setaria faberii*, and *Plantago lanceolata*.

45. The method of claim 29 wherein a seed of said plant is contacted with said effective amount.

46. The method of claim 29 wherein said plant is contacted with said effective amount by application of said effective amount to the medium in which said plant is growing.

47. The method of claim 46 wherein said plant is growing in soil.

48. The method of claim 29 wherein said plant is contacted with said effective amount by application of said effective amount to the roots of said plant.

* * * * *